(12) United States Patent
Mahon et al.

(10) Patent No.: US 7,171,037 B2
(45) Date of Patent: Jan. 30, 2007

(54) OPTICAL INSPECTION SYSTEM AND METHOD FOR DISPLAYING IMAGED OBJECTS IN GREATER THAN TWO DIMENSIONS

(75) Inventors: James Mahon, Dublin (IE); S. Jeffrey Rosner, Palo Alto, CA (US); Izhak Baharav, San Jose, CA (US); Xuemei Zhang, Mountain View, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 712 days.

(21) Appl. No.: 10/393,413

(22) Filed: Mar. 20, 2003

(65) Prior Publication Data

US 2004/0184032 A1   Sep. 23, 2004

(51) Int. Cl.
*G06K 9/00* (2006.01)
*G06K 9/68* (2006.01)

(52) U.S. Cl. ............... 382/145; 382/154; 382/218
(58) Field of Classification Search ........... 382/145, 382/149–150, 154, 218, 309, 311; 345/419; 348/87; 356/237.4
See application file for complete search history.

(56) References Cited

U.S. PATENT DOCUMENTS

| | | | |
|---|---|---|---|
| 4,561,731 A * | 12/1985 | Kley ........................... 349/1 |
| 4,677,473 A | 6/1987 | Okamoto et al. |
| 5,032,735 A | 7/1991 | Kobayashi et al. ......... 250/572 |
| 5,166,185 A * | 11/1992 | House et al. ............... 521/159 |
| 5,245,671 A | 9/1993 | Kobayashi et al. ............ 382/8 |
| 5,455,870 A | 10/1995 | Sepai et al. |
| 5,720,018 A * | 2/1998 | Muller et al. ............... 345/581 |
| 5,760,893 A | 6/1998 | Raymond ................... 356/237 |
| 6,023,663 A | 2/2000 | Kim |
| 6,111,602 A | 8/2000 | Kim |
| 6,177,682 B1 | 1/2001 | Bartulovic et al. |
| 6,207,946 B1 | 3/2001 | Jusoh et al. ............. 250/208.1 |
| 6,219,461 B1 | 4/2001 | Wallack |
| 6,273,338 B1 | 8/2001 | White ..................... 235/462.42 |
| 6,323,942 B1 | 11/2001 | Bamji ......................... 356/5.01 |
| 6,362,877 B1 | 3/2002 | Kobayashi et al. ....... 356/237.5 |
| 6,512,838 B1 | 1/2003 | Rafii et al. .................. 382/106 |
| 6,515,740 B2 | 2/2003 | Bamji et al. ............. 356/141.1 |
| 6,758,384 B2 * | 7/2004 | Kim et al. .................. 228/102 |
| 2002/0179679 A1 | 12/2002 | Kim et al. |
| 2003/0025906 A1 | 2/2003 | Sheffer ..................... 356/237.5 |

FOREIGN PATENT DOCUMENTS

DE       10128160      6/2001
EP        0443289     12/1990

OTHER PUBLICATIONS

Yoshimura, et al "A three dimensional sensor for automatic visual inspection of soldered parts", IEEE, pp. 562-567, 1995.*

(Continued)

*Primary Examiner*—Daniel Mariam

(57) ABSTRACT

A display for use in a printed circuit board inspection system for inspecting objects on a printed circuit board is capable of displaying a greater-than-two dimensional image of the shape of the surface of an object resident on the printed circuit board in at least two dimensions. The image of the object is generated based on optical imaging of the object under different illumination configurations.

21 Claims, 14 Drawing Sheets

OTHER PUBLICATIONS

Shree K. Nayar; "*Shape and Reflectance from Image Intensities*"; Intelligent Robotic Systems for Space Exploration; 1991 Proceedings; 1991 Third Annual Conference; Nov. 18-19, 1991; pp. 81-98.

Robert J. Woodham; "*Gradient and Curvature from the Photometric-Stereo Method, Including Local Confidence Estimation*"; J. Opt. Soc. Am. A, vol. 11, No. 11; Nov. 1994; pp. 3050-3068.

Shree K. Nayar; "*Shape Recovery Methods for Visual Inspection*"; Applications of Computer Vision, Proceedings, 1992; IEEE Workshop; Nov. 30-Dec. 2, 1992; pp. 136-145.

Howard Schultz; "*Retrieving Shape Information from Multiple Images of a Specular Surface*"; IEEE Transactions on Pattern Analysis and Machine Intelligence, vol. 16, No. 2; Aug. 1994; pp. 195-201.

Ruo Zhang, Ping-Sing Tsai, James Edwin Cryer, and Mubarak Shah; "*Shape from Shading: A Survey*"; IEEE Transactions on Pattern Analysis and Machine Intelligence, vol. 21, No.; Aug. 1999; pp. 690-705.

Shree K. Nayar, Xi-Sheng Fang, and Terrance Boult; "*Removal of Specularities Using Color and Polarization*"; Proceedings CVPR '93; 1993 IEEE Computer Society Conference; Jun. 15-17, 1993; pp. 583-590.

David H. Brainard; "*An Ideal Observer for Appearance: Reconstruction from Samples*"; UCSB Vision Labs Tech Report 95-1, Department of Psychology, UC Santa Barbara, Santa Barbara, CA; Dec. 1995; pp. 1-19.

Fredric Solomon and Katsushi Ikeuchi; "*Extracting the Shape and Roughness of Specular Lobe Objects Using Four Light Photometric Stereo*"; IEEE Transactions on Pattern Analysis and Machine Intelligence, vol. 18, No. 4, Aug. 1996; pp. 449-454.

Robert T. Frankot and Rama Chellappa; "*A Method for Enforcing Integrability in Shape from Shading Algorithms*"; IEEE Transactions on Pattern Analysis and Machine Intelligence, vol. 10, No. 4; Jul. 1988; pp. 439-451.

The Imaging Source; Structured Light; www.theimagingsource.com/prod/light/light_bg.struc.htm; pp. 7-9.

David H. Brainard; "*Bayesian Method for Reconstructing Color Images from Trichromatic Samples*"; Proceedings of the IS&T 47th Annual Conference/ICPS; Rochester, New York; 1994; pp. 375-380.

David H. Brainard and Doron Sherman; "*Reconstructing Images from Trichromatic Samples: From Basic Research to Practical Applications*"; Proceedings of the 3rd IS&T/SID Color Imaging Conference; Scottsdale, Arizona; 1995; pp. 4-10.

Rudolf Schwarte, Gerd Häusler, and Reinhard W. Maiz; "*Computer Vision and Applications: A Guide for Students and Practitioners*"; Chapter 7, Three-Dimensional Imaging Techniques; Academic Press; 2000; pp. 177-208.

Tae-Hyeon Kim; Tai-Hoon Cho; Young-Shik Moon and Sung-Han Park; "*An Automated Visual Inspection of Solder Joints Using 2D and 3D Features*"; IEEE May 1996; pp. 110-115.

International Search Report dated Jul. 22, 2004.

* cited by examiner

OPTICAL INSPECTION SYSTEM AND METHOD FOR DISPLAYING IMAGED OBJECTS IN GREATER THAN TWO DIMENSIONS

CROSS-REFERENCE TO RELATED APPLICATIONS

This U.S. Nonprovisional Application for Patent is related by subject matter to copending and commonly assigned U.S. Nonprovisional Application for Patent Ser. Nos. 10/392,758, 10/392,990 and 10/392,948. U.S. Nonprovisional Application for Patent Ser. Nos. 10/392,758, 10/392,990 and 10/392,948 are hereby incorporated by reference in their entirety.

BACKGROUND OF THE INVENTION

1. Technical Field of the Invention

The present invention relates generally to the field of optical inspection systems. More particularly, the present invention relates to systems and methods for displaying imaged objects in greater than two dimensions.

2. Description of Related Art

In conventional optical inspection systems, the data collected produces a two-dimensional image of a three-dimensional object. For example, in optical inspection of printed circuit boards (PCBs), the data collected produces a two-dimensional image of the object surface. Although a number of techniques for reconstructing a three-dimensional image from multiple two-dimensional images known are in the computer vision industry, these techniques have not been applied to the printed circuit board optical inspection industry due to the difficulty in processing the specular reflections off shiny specular objects, such as solder joints and other components present or PCBs.

Therefore, in conventional optical inspection systems, a determination of whether an object is defective is made by manually analyzing the two-dimensional image of the object surface. The manual inspection process is labor-intensive and prone to errors. In many cases, two-dimensional images do not provide enough information to accurately assess whether or not an object is defective.

Therefore, what is needed is an optical inspection system capable of displaying an image of an object in greater than two dimensions to improve the accuracy in the detection of defective objects on printed circuit boards.

SUMMARY OF THE INVENTION

Embodiments of the present invention provide a printed circuit board inspection system for inspecting objects on a printed circuit board that is capable of displaying a greater-than-two dimensional representation of the shape of the surface of an object resident on the printed circuit board. The representation is displayed in at least two dimensions. The image of the object is generated based on an optical imaging of the object under different illumination configurations.

In one embodiment, the inspection system is designed to display only images of objects that may be defective. For example, specification data associated with the object can be compared with object features estimated from the image, and the image can be selectively displayed based on the results of the comparison. In further embodiments, the inspection system can be configured to receive instructions for altering the displayed image and manipulate, for example, the viewing angle of the object, based on the instructions.

The ability to display an image of the inspected object in greater than two dimensions can improve the user accuracy in detecting defective objects by providing more information to the user about the shape of the object. Furthermore, the invention provides embodiments with other features and advantages in addition to or in lieu of those discussed above. Many of these features and advantages are apparent from the description below with reference to the following drawings.

BRIEF DESCRIPTION OF THE DRAWINGS

The disclosed invention will be described with reference to the accompanying drawings, which show important sample embodiments of the invention and which are incorporated in the specification hereof by reference, wherein.

DETAILED DESCRIPTION OF THE EXEMPLARY EMBODIMENTS

The numerous innovative teachings of the present application will be described with particular reference to the exemplary embodiments. However, it should be understood that these embodiments provide only a few examples of the many advantageous uses of the innovative teachings herein. In general, statements made in the specification do not necessarily delimit any of the various claimed inventions. Moreover, some statements may apply to some inventive features, but not to others.

Figure 1:
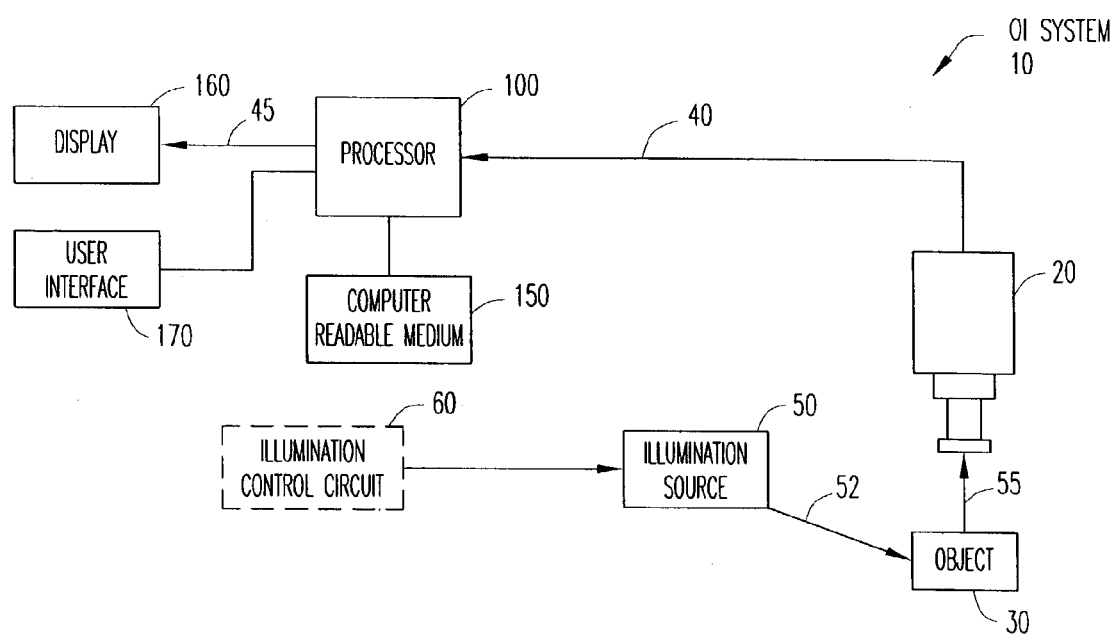
FIG. 1 is a block diagram illustrating an optical inspection system in accordance with embodiments of the present invention.

Referring now to FIG. 1, there is illustrated a simplified schematic of an optical inspection (OI) system 10 capable of rendering a three-dimensional image 45 of the surface of an object 30, which can have both specular and diffuse surface reflection elements, in accordance with embodiments of the present invention. The OI system 10 includes an illumination source 50 for illuminating the surface of an object 30 and a sensing apparatus (e.g., camera) 20 for capturing an image of the surface of the object 30 within the field-of-view (FOV) of the camera 20. For example, in the simplified OI system 10 shown in FIG. 1, illumination 52 (e.g., light) emitted from the illumination source 50 is reflected off a portion of the surface of the object 30 and received by the camera 20. The reflected illumination (e.g., light) 55 can be specular, diffuse or a combination of specular and diffuse. As used herein, the term specular refers to a sharply defined light beam reflecting off a smooth surface, where the surface acts as a mirror, and the reflected beam emerges in only one direction determined by the angle of incidence of the incident light, and the term diffuse refers to reflection from a rough surface in which the reflected light emerges in all directions.

The illumination source 50 can be any suitable source of illumination 52. For example, the illumination source 50 can include one or more light-emitting elements, such as one or more point light sources, one or more collimated light sources, one or more illumination arrays, such as one or more circular arrays of light-emitting diodes, or any other illumination source suitable for use in OI systems 10. The illumination intensity can be constant, or in some embodiments, the intensity of the illumination 52 emitted by one or more of the light-emitting elements within the illumination source 50 can be controlled by an illumination control circuit 60. In addition, the wavelength of the illumination 52 emitted by the illumination source 50 can be controlled by the illumination control circuit 60 and/or chosen based on a number of factors, including manufacturer preferences. For example, some manufacturers may prefer green light or blue light to red light in certain applications. Examples of illumination sources 50 are shown in more detail in FIGS. 2–12.

One application of OI systems 10 is the inspection of solder joints on printed circuit boards. In many solder joint test systems, the illumination source 50 and camera 20 are attached together and jointly connected to an X,Y motorized gantry (not shown), which forms at least a part of a machine vision apparatus. The printed circuit boards are transferred into the OI system 10 by a conveyor belt (not shown), and the gantry is used to move the camera 20 to view selected objects 30 (e.g., solder joints) on the printed circuit boards. In other systems, the camera 20 and illumination source 50 are fixed and the printed circuit boards are moved into position. The OI system 10 analyzes the light that is specularly and/or diffusely reflected from the surfaces of the solder joints to determine whether all of the component leads have been soldered correctly.

To analyze the reflected light 55, image data 40 representing the two-dimensional images recorded by the camera 20 are passed to a processor 100 to perform a three-dimensional (or in other embodiments, a greater than two-dimensional) reconstruction of the shape of the surface of the object 30. The processor 100 can be a microprocessor, microcontroller, or other type of processing device capable of performing the functions described herein. In addition, the processor 100 can include multiple processors or be a single processor having one or more processing elements (referred to herein as separate processors).

Raw pixel values representing at least one illumination parameter, such as the illumination intensity and/or spectral characteristics, of the reflected light 55 captured in the two-dimensional images recorded by the camera 20 are used by the processor 100 to determine surface gradients of the object surface 30. Each surface gradient is a vector defining the slope of the object surface at a given spatial location, and includes information identifying both the surface tilt, which refers to the angle between the surface normal vector and the vector orthogonal to the plane in which the object is located, and the surface orientation, which refers to the direction that the surface is facing.

From the surface gradient information, the processor 100 can reconstruct a three-dimensional image 45 of the shape of the object surface by finding a set of surface heights that are consistent with the surface gradient information. The reconstructed three-dimensional image 45 can be stored in a computer-readable medium 150 for later processing or display. For example, the computer-readable medium 150 can be a memory device, such as a disk drive, random access memory (RAM), read-only memory (ROM), compact disk, floppy disk or tape drive, or any other type of storage device.

The three-dimensional image 45 of the object 30 can be displayed to a user of the OI system 10 on a display 160. The display 160 can be a three-dimensional display, such as a sharp screen, 3-D ball, user glasses (e.g., 3-D glasses or virtual reality glasses), or other type of three-dimensional display. In other embodiments, the display 160 can be a "rocking" two-dimensional display that uses a rocking motion of the image 45 to rotate the image 45 to create a three-dimensional image in the mind of the observer. The rocking can be automatic or controlled by a user. In further embodiments, the display 160 can be a two-dimensional display that displays a two-dimensional projection of the three-dimensional image 45 and that allows the user to rotate the angle of viewing to view the complete three-dimensional image. The viewing angle can be manipulated through a user interface 170, such as a joystick, virtual reality interface or other type of control. In addition, the user interface 170 can enable the user to control the information presented on the display 160. For example, through the user interface 170, the user can select only certain portions of the image 45 to be displayed in 3-D.

Figure 2:
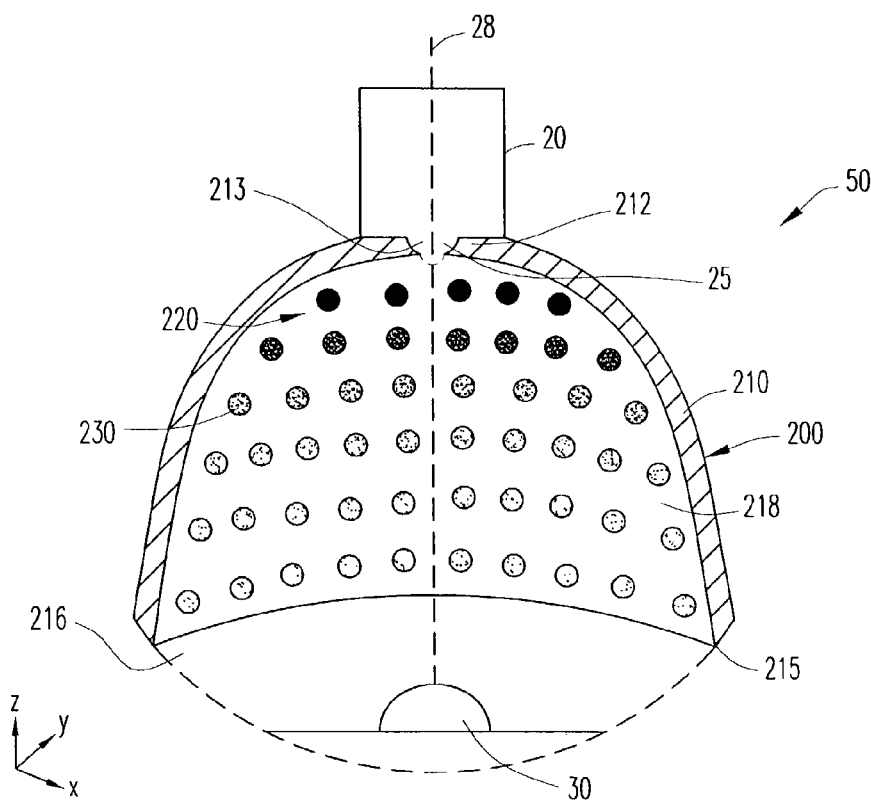
FIG. 2 is a cut away view of a lighting ring capable of producing lighting gradients in accordance with one embodiment of the invention.

One example of an illumination source 50 is shown in FIG. 2. The illumination source 50 includes a light ring 200 containing circular arrays 220 of light-emitting elements 230 (e.g., light-emitting diodes) arranged concentrically about a central axis 28 of an aperture 25 of the camera 20. The axis 28 is orthogonal to the plane (x, y) in which the object 30 is located. The number of illumination arrays 220 is a function of the desired angular separation between the illumination arrays 220.

The light-emitting elements 230 are shown mounted on an inside surface 218 of a dome-shaped support structure 210. The support structure 210 further has a top surface 212 with an opening 213 of an area at least equivalent to the area of the aperture 25 of the camera 20 and a bottom surface 215 with an opening 216 sufficient in diameter to allow the light emitted from the light-emitting elements 230 to illuminate the surface of the object 30 placed under the support structure 210. The light ring 200 and camera 20 can be suitably mounted together on a machine vision apparatus that is capable of moving the light ring 200 and camera 20 into a position that the desired object 30 can be fully illuminated by the light ring 200 within the FOV of the camera 20.

The light ring 200 is designed to illuminate the object 30, such that at least one illumination parameter has an illumination gradient with respect to that illumination parameter. For example, the illumination parameter can be the illumination intensities of the light-emitting elements 230 and/or the spectral characteristics of the light-emitting elements 230. In the embodiment shown in FIG. 2, the illumination intensities of the individual light-emitting elements 230 in the light ring 200 are capable of varying gradually in order to produce an illumination intensity gradient sufficient to enable the surface gradient at a particular spatial (x,y,z) location on the surface of the object 30 to be estimated from the intensity of the specularly reflected light from that spatial location.

The location of the light-emitting elements 230 on the inside surface 218 of the dome-shaped structure 210 will be defined herein using the celestial navigation-based terms of elevation, which is measured between the vector orthogonal to the x-y plane in which the object is located and the vector pointing from the center of the field of view of the camera 20 to the light-emitting element 230 position, and azimuth, which is measured in the x-y plane between the y-axis and the vector pointing from the center of the field of view of the camera 20 to the light-emitting element 230 position. For example, as shown in FIG. 2, the illumination intensity can be varied to produce an illumination gradient in elevation of the light ring 200 in the z-direction along the direction of the axis 28. Thus, the light-emitting elements 230 within the center illumination array 220 nearest the top opening 213 have the lowest intensity and the light-emitting elements 230 within the peripheral illumination array 220 nearest the bottom opening 216 have the highest intensity. It should be understood that in other embodiments, the illumination intensity gradient can be reversed. It should also be understood that numerous other illumination gradients can be achieved, depending on the user or manufacturer preferences. In addition, other examples of illumination gradients based on intensity and/or spectral characteristics are described below and shown in FIGS. 4A, 4B, 5A–5C and 7.

Figure 3:
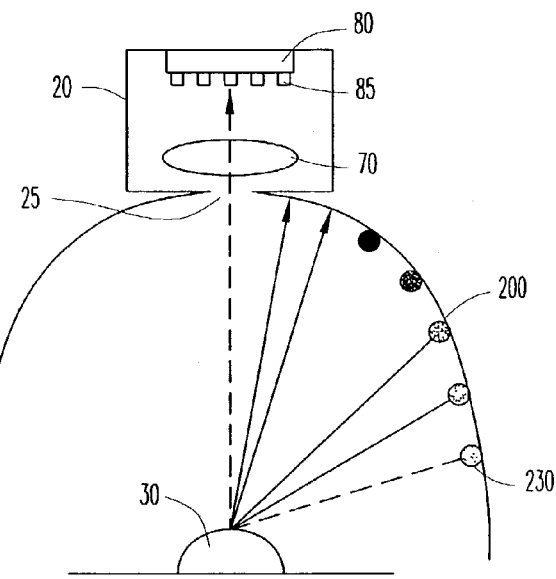
FIG. 3 is a simplified pictorial representation of the relationship between the lighting angle and the reception at the camera of light reflected off a specular surface of an object.

Referring now to FIG. 3, the camera 20 includes a sensor 80 that can produce image data (e.g., raw pixel values) that represent the intensity of the reflected light. When the camera 20 captures an image of the surface of the specular object 30, the image contains contributions from a range of light-emitting element 230 locations on the light ring 200. The extent of this range of locations depends on such factors as the focal length, magnification and f-number of the lens, and the distance between the object 30 and the light ring 200. Each of the light-emitting elements contributing to the captured image can be considered one of the source light-emitting elements 230. The light from the source light-emitting elements 230 contained inside of this range of locations is integrated together in the image, causing blurring. However, since the illumination intensities vary linearly with incidence angle, the average value of the intensity is unaffected by blurring except at the ends of the incidence angle range between illumination arrays 220. Therefore, the surface gradient measurements, which are determined from the average intensity of the image, are also unaffected by blurring. In fact, some blurring may even be advantageous by obviating the need for light diffusing filters in the light ring 200.

The intensity of the actual received reflected light depends on other factors, such as the surface reflectivity and the distance between the object 30 and the source light-emitting element 230. The amount of information that is available in a single image may be insufficient to account for these factors. Therefore, in some embodiments, a single image under a fixed illumination gradient may not be adequate to measure the surface gradients of the object 30. In this case, two or more images under different illumination gradients can be used in order to reduce the sensitivity of the measurements to the reflectivity of the surface of the object 30, or to the area of the object surface that has a particular surface gradient. For example, the undesired sensitivities can be normalized out by dividing corresponding pixel values from pairs of images collected under different illumination gradients. The surface gradients could be determined by relating the measured ratio values in the image to the intensity characteristics of the source light-emitting elements 230.

The uncertainty in the measured surface gradient is also dependent in part on the size of the aperture 25. If the lighting pattern is spatially varied continuously, the highest possible measurement precision occurs when the aperture 25 is infinitely small. However, with a pinhole aperture 25, a limited amount of light enters the camera 20, and therefore, a longer exposure is needed, resulting in additional camera noise. Therefore, the size of the aperture 25 chosen can be a trade-off between the level of noise in camera measurements and the level of built-in uncertainty in surface gradient measurement.

Figure 10A:
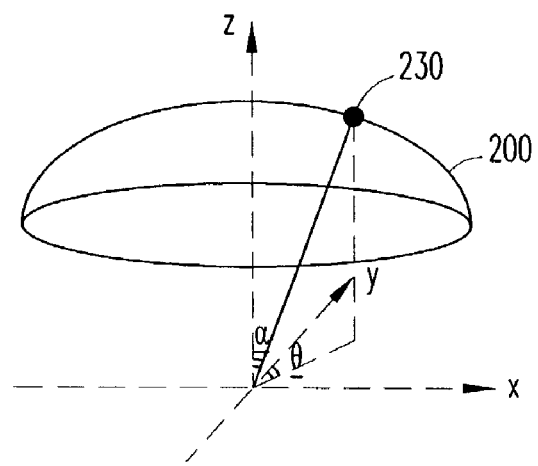
FIGS. 10A and 10B are graphical representations of the geometrical determination of the surface gradient based on lighting angles.
Figure 10B:
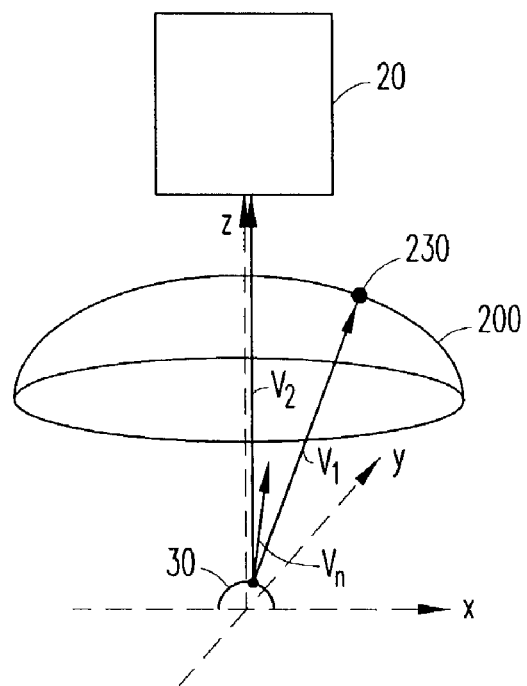

In general, as shown in FIGS. 10A and 10B and with reference to FIG. 3, the surface gradient of the object 30 at a particular spatial location on the surface of the object 30 is determined from the geometrical relationship between the angle of incidence of light illuminating the surface at that spatial location and the angle of reflection of the light that passes through the aperture 25 and into the sensor 80 of the camera 20 via a lens 70. The angle of reflection is known based on the relative position between the sensor 80 and the object 30. From the recorded light level at a pixel 85 or group of pixels 85 corresponding to that spatial location of the object, the identity of the source light-emitting element 230 can be determined. A simple geometrical calculation determines the surface gradient that would direct light from that source light-emitting element 230 to the pixel 85.

FIGS. 10A and 10B are graphical representations of the calculation of the surface gradient from the measured illumination intensity using a normalizing image. A normalizing image is an additional image of the object captured with all of the light-emitting elements set at the maximum (brightest) intensity. If $X_i$ represents the pixel value for a particular image location when the image is captured under lighting configuration i and $X_0$ represents the pixel value of the same image location when the image is captured under uniform lighting with an illumination intensity level $k_0$, then the illumination intensity level corresponding to $X_i$ is:

$$L_1 = X_i/X_0 * k_0. \quad \text{(Equation 1)}$$

For example, in the elevationally-varying illumination gradient configuration shown in FIG. 4A, as will be described in more detail below, the illumination configuration has an illumination intensity level of:

$$L_1 = \alpha/(\pi/2) * k_0, \quad \text{(Equation 2A)}$$

where $\alpha$ is the elevation, measured between the vector orthogonal to the object plane and the vector pointing from the center of the field of view to the light-emitting element position. In azimuthally-varying illumination gradient configurations of the type shown in FIG. 4B, which will be described in more detail below, the illumination configuration has an illumination intensity of:

$$L_2 = \theta/(2\pi) * k_0, \quad \text{(Equation 2B)}$$

where $\theta$ is the azimuth measured in the x-y plane between the y-axis and the vector pointing from the center of the field of view of the camera 20 to the light-emitting element 230 position. Therefore, from the image values $X_1$, $X_2$, and $X_0$:

$$\alpha = X_1/X_0 * \pi/2, \; \theta = X_2/X_0 * 2\pi. \quad \text{(Equation 3)}$$

With other illumination configurations, the elevation and azimuth can be similarly solved from image pixel values. Once the elevation and azimuth of the source light-emitting element is determined from the recorded illumination intensity, the surface normal of the corresponding spatial location on the object can be solved. For example, as shown in FIG. 10B, if $\vec{V}_1$ represents a unit vector pointing from the spatial location (x,y,z) on the object to the source light-emitting element, and $\vec{V}_2$ represents a unit vector pointing from the spatial location (x,y,z) to the camera, then the surface normal vector at this pixel position $\vec{V}_n$ is the vector sum of $\vec{V}_1$ and $\vec{V}_2$, as follows:

$$\vec{V}_n = \vec{V}_1 + \vec{V}_2. \quad \text{(Equation 4)}$$

The surface normal vector represents the surface gradient at the spatial location (x,y,z) of the object.

Referring again to FIG. 2, the elevational illumination gradient shown in FIG. 2 is sufficient to estimate the surface tilt at a particular spatial location on the surface of the object. However, to reconstruct a three-dimensional image, it is important to also know the surface orientation at that spatial location. For example, if the surface tilt at a particular spatial location of the object 30 is determined to be 20 degrees, but the sloping direction of the object 30 at that spatial location is unknown, then the surface gradient is unknown. To determine the orientation of the surface gradient, the azimuthal position of the source light-emitting element 230 within the illumination array 220 around the axis 28 should additionally be ascertained.

The surface orientation can be identified by using a different illumination gradient that varies the illumination intensity of the individual light-emitting elements 230 azimuthally within each illumination array 220. For example, as shown in FIGS. 4A and 4B, when using a monochrome camera, a full determination of the positions (i.e., elevation and azimuth) of light-emitting elements 230 can be obtained using two images taken under different illumination intensity gradients. FIGS. 4A and 4B are top-down views of the light ring 200 showing the illumination intensity gradients and the azimuthal position of each of the light-emitting elements 230 circumferentially around the axis. It should be understood that the azimuthal positions in FIG. 4B have been arbitrarily set for illustrative purposes only.

Figure 4A:
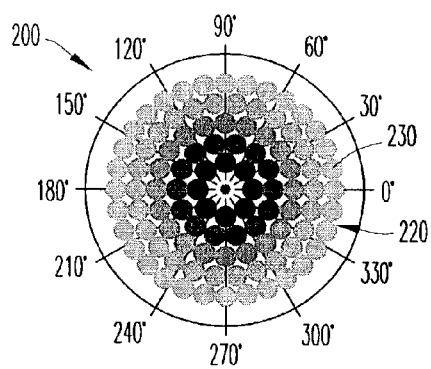
FIGS. 4A and 4B are top views of the light ring showing different lighting gradients in one embodiment for capturing both the surface gradient and the orientation.
Figure 4B:
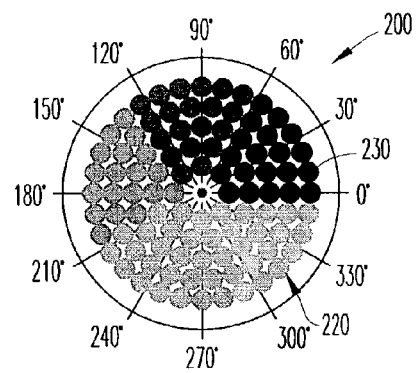

In a first image taken under the illumination configuration shown in FIG. 4A, the illumination intensity of the light-emitting elements 230 varies between illumination arrays 220 with respect to the elevation of the illumination arrays 220, as described above in connection with FIG. 2, to estimate the surface tilt of the object. In a second image taken under the illumination configuration shown in FIG. 4B, the illumination intensity of the light-emitting elements 230 varies azimuthally within each illumination array 220. For example, as shown in FIG. 4B, the illumination intensity of the light-emitting elements 230 varies azimuthally around the axis to produce a clockwise illumination gradient. Thus, the light-emitting element 230 within each illumination array 220 positioned at 0 degrees azimuth has the highest intensity and the intensity of the light-emitting elements 230 within each illumination array 220 gradually decreases azimuthally from 360 degrees to 0 degrees, with the light-emitting element 230 within each illumination array 220 positioned closest to 1 degrees azimuth having the lowest intensity. It should be understood that in other embodiments, the azimuthal illumination gradient can be counter-clockwise.

From the intensity of the light reflected from the surface of the object 30, the azimuthal position of the source light-emitting element 230 within the illumination array can be determined. Combined with the previously measured elevation of the illumination array 220 of the source light-emitting element 230, the particular source light-emitting element 230 within the illumination array 220 can be determined. Once the particular source light-emitting element 230 is identified, the surface gradient can be measured. However, with only two images, the direction of measurement encoding is not spatially smooth due to the abrupt change from dark to light at 0 degrees. The abrupt change in lighting intensity can cause uncertainty in the direction of measurement at 0 degrees when the aperture is large, or when the image is not adequately focused.

Figure 5A:
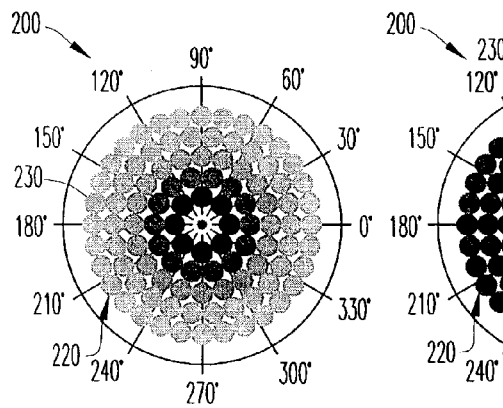
FIGS. 5A–5C are top views of the light ring showing different lighting gradients in another embodiment for capturing both the surface gradient and the orientation.
Figure 5B:
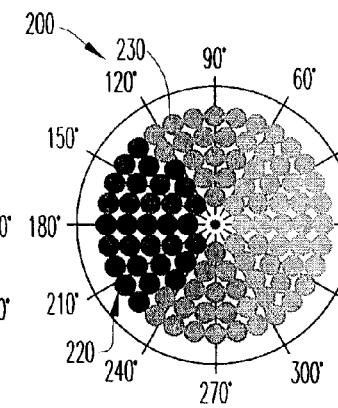
Figure 5C:
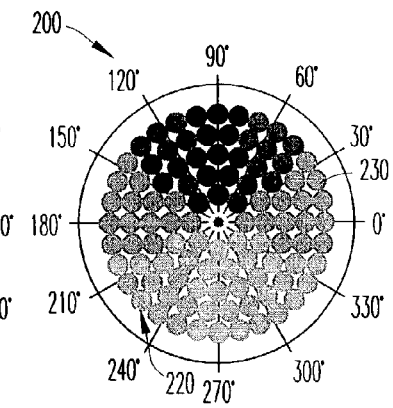

Therefore, referring now to FIGS. 5A–5C, in other embodiments, the surface gradient can be estimated using image data captured in three images. In a first image taken under the illumination configuration shown in FIG. 5A, the illumination intensity of the light-emitting elements 230 varies between illumination arrays 220 with respect to the elevation of the illumination arrays 220, as described above in connection with FIG. 2, to estimate the surface tilt of the object. In second and third images taken under the illumination configurations shown in FIGS. 5B and 5C, respectively, the illumination intensity of the light-emitting elements 230 varies azimuthally within each illumination array 220. However, unlike FIG. 4B, the direction of measurement coding in FIGS. 5B and 5C is spatially smooth, and thus more tolerant of image blurring.

As can be seen in FIG. 5B, the light-emitting element 230 within each illumination array 220 positioned at 0 degrees azimuth has the highest intensity and the intensity of the light-emitting elements 230 within each illumination array 220 gradually decreases azimuthally in both directions from 0 degrees, with the light-emitting element 230 within each illumination array 220 positioned closest to 180 degrees azimuth having the lowest intensity. From the intensity of the light reflected from the surface of the object 30, two potential azimuthal positions of the source light-emitting element 230 within the illumination array 220 are identified. To resolve the ambiguity in the azimuthal position from which the light is reflected, a third image is taken under the illumination gradient shown in FIG. 5C. In FIG. 5C, the illumination gradient is rotated 90 degrees from the illumination gradient in FIG. 5B so that the light-emitting element 230 within each illumination array 220 positioned at 270 degrees azimuth has the highest intensity and the intensity of the light-emitting elements 230 within each illumination array 220 gradually decreases azimuthally in both directions from 270 degrees, with the light-emitting element 230 within each illumination array 220 positioned at 90 degrees azimuth having the lowest intensity.

A surface gradient can be estimated for each pixel by combining the surface tilt measurement, the two surface orientation measurements, and the location of the measured pixel relative to the center of the camera field of view. The estimated surface gradients can be combined to reconstruct a three-dimensional shape of the specular object.

However, since some surfaces are partly specular, it may be difficult to separate the specular and diffuse parts of the image. Therefore, in additional embodiments, to separate the specular areas, an additional image of the object is captured with all of the light-emitting elements set at a uniform illumination. Under uniform illumination, the specular areas of the object will appear much brighter than the diffuse areas, enabling the specular areas to be separated from the diffuse areas for later image processing. This additional image can also be used as a normalizing factor, as described above in connection with FIGS. 10A and 10B, to establish the pixel value corresponding to a reflection from the brightest light source. This additional image increases the total number of images per object to three or four, depending on the illumination gradient configurations used. However, even with the additional image, the amount of information obtained in the images greatly outweighs the amount of information obtained in the same number of images taken with a traditional ring lighting scheme.

Figure 6:
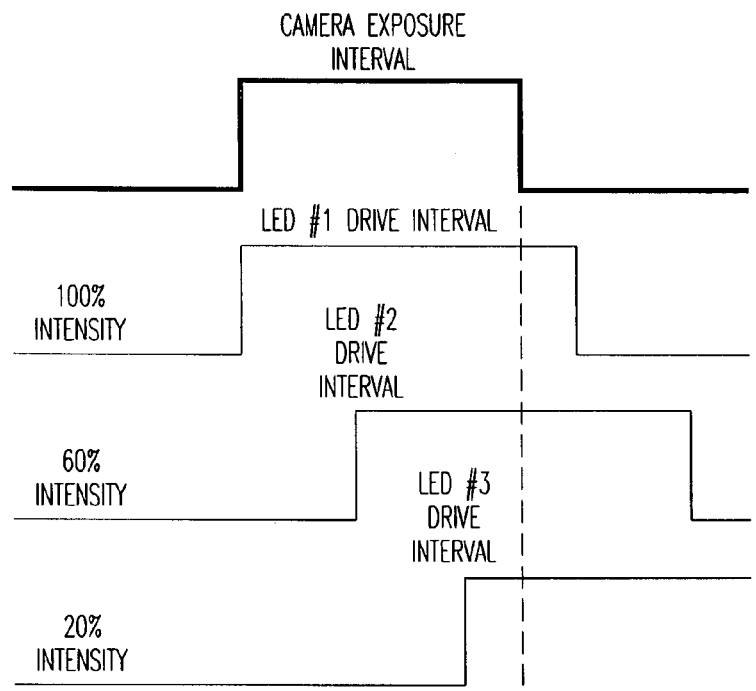
FIG. 6 is a timing diagram illustrating the drive interval of light-emitting diodes (LEDs) with respect to the camera exposure interval to control the intensity of light received at the camera from the various LEDs.

One example of the output of an illumination control circuit 60 (shown in FIG. 1) that is capable of varying the illumination intensity of an array of photodiodes to obtain an illumination intensity gradient is shown in FIG. 6. The illumination intensity between photodiodes (e.g., LEDs) is varied by pulsing the LEDs in the array. The intensity of the LEDs is proportional to the overlap of their electrical drive pulses with respect to the exposure time interval of the camera. As can be seen in FIG. 6, the apparent intensity between two LEDs depends on the overlap between the drive time intervals of the LEDs, and not just on the duration that the LED is active. It should be understood that the type of illumination control circuit used to vary the illumination intensity is not limited to the type of illumination control circuit in FIG. 6, and any method of creating lighting variations and/or illumination gradients may be used.

Figure 7:
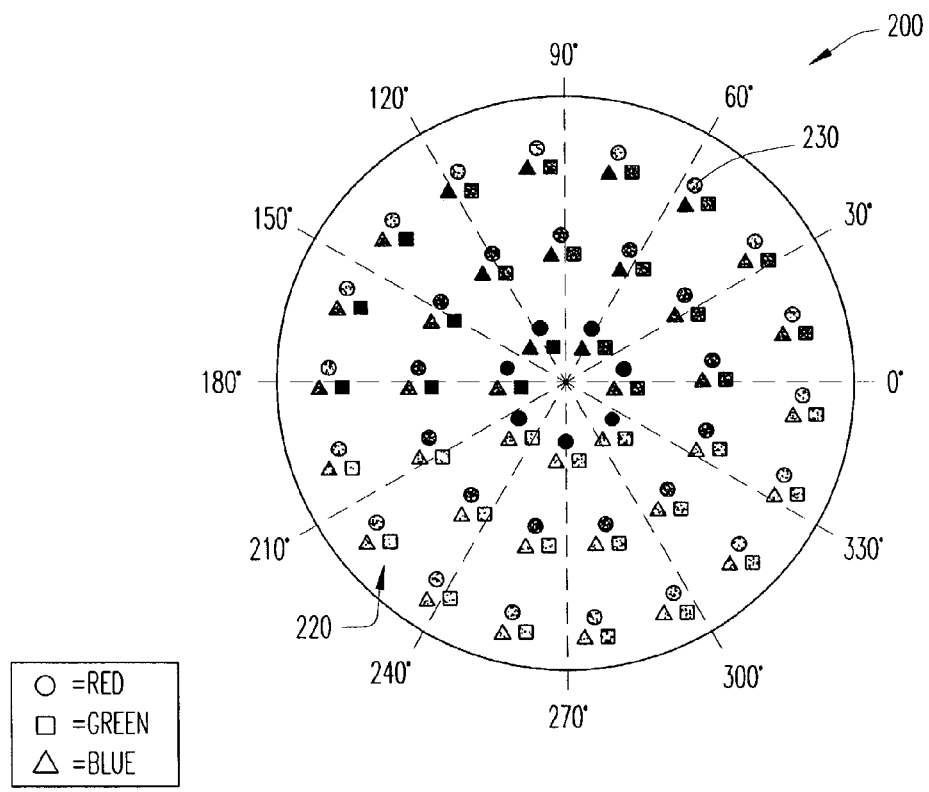
FIG. 7 is a top view of the light ring showing a colored lighting gradient for capturing both the surface gradient and the orientation.

Referring now to FIG. 7, the number of images can be reduced by using a color camera and light-emitting elements 230 (e.g., LEDs) of several different colors in the light ring 200. The LEDs can be configured to create gradation in the illumination color (i.e., spectral characteristics) as a function of elevation and/or azimuth. For example, a triad of LEDs of different colors can be substituted for each of the single-color LEDs of FIG. 2. The color variation of the inside of the light ring 200 could resemble a rainbow or a color gamut plot. Therefore, in the embodiment shown in FIG. 7, the illumination gradient is an illumination wavelength gradient. A single image capture can be used to collect all of the information required for reconstruction of the shape of the object.

For example, as shown in FIG. 7, the intensities of the red LEDs vary in elevation between illumination arrays 220 in the light ring 200 to measure the surface tilt, while the green and blue LED intensities vary azimuthally within the illumination arrays 220 of the light ring 200 to identify the surface orientation. Specifically, the illumination intensity of the green LED within each illumination array 220 positioned at 0 degrees azimuth has the highest intensity and the intensity of the green LEDs within each illumination array 220 gradually increases azimuthally in both directions from 0 degrees, with the green LED within each illumination array 220 positioned closest to 180 degrees azimuth having the lowest intensity. The illumination gradient of the blue LEDs is rotated 90 degrees from the illumination gradient of the green LEDs so that the blue LED within each illumination array 220 positioned at 90 degrees azimuth has the highest intensity and the intensity of the blue LED within each illumination array 220 gradually increases azimuthally in both directions from 90 degrees, with the blue LED within each illumination array 220 positioned closest to 270 degrees azimuth having the lowest intensity. In this way, the data from all three images previously required using a single-color (white, red, blue, green, etc.) illumination source can be obtained in a single image. It should be understood that numerous variations on the color illumination gradients described above are possible to produce image data corresponding to the image data obtained from the illumination gradients shown in FIGS. 4A and 4B and/or FIGS. 5A–5C.

Figure 8:
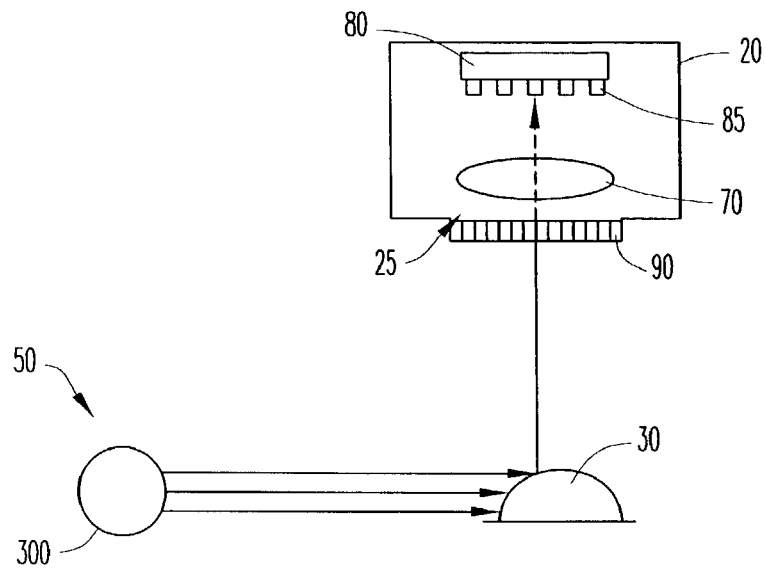
FIG. 8 is a simplified pictorial representation of an optical inspection system capable of modifying the grayscales of the light received at the camera based on the angle of entrance into the camera, in accordance with other embodiments of the present invention.

In other embodiments, instead of creating an illumination gradient by defining the intensities of the light-emitting elements themselves, as shown in FIG. 8, the illumination gradient can be created near the camera 20 using an optical element 90. Thus, as used herein, the term illumination gradient refers to either an illumination gradient created by the light-emitting elements having different intensities as described above or to an effective illumination gradient produced by filtering the reflected light. Even though light reflected from a large range of surface gradients can enter the camera 20, the reflected light enters the camera 20 at different locations in the camera aperture 25. Therefore, the optical element 90, for example, can be a patterned or directionally-selective aperture window 25 of the camera 20, such that light entering at different locations of the aperture 25, or entering the aperture 25 at different angles, will have different gray scales, or levels of illumination intensity at the sensor 80.

In other embodiments, as shown in FIG. 8, the optical element 90 can be a patterned (or directionally-selective) filter or plate 90 attached to the camera 20 near the aperture 25 to produce different gray levels for reflected light rays entering the aperture 25 from different angles. The plate 90 can be a piece of stained glass or plastic that is either uniform, or has a shading pattern across the field. If the plate 90 is a uniform piece of stained glass or plastic, light that enters at a non-zero angle of incidence with respect to the normal to the surface of the plate 90 has a longer path length through the plate 90, and therefore, is absorbed more than light that enters at zero angle of incidence. For large angles of incidence, a larger proportion of the reflected light is reflected back or absorbed compared to smaller angles of incidence.

When using an optical element 90 to create the illumination gradient, the angle of reflection can be determined from the recorded intensity. Therefore, the angle of incidence of the illumination source 50 should be held constant in order to determine the surface gradient. In addition, to capture sufficient information to estimate the surface gradients across the whole surface of the object, multiple images (e.g., four or more) under illumination from different angles of incidence may be required. For example, as shown in FIG. 8, the illumination source 50 can include four or more light sources 300, only one of which is shown for simplicity, producing light in four different directions. In one embodiment, the light sources 300 can include collimated light sources (e.g., parallel light coming in from four different directions, in four sequential captures). In other embodiments, the light sources 300 can include point sources in each of four directions (e.g., separate single LEDs illuminating from different directions, in four sequential captures). Since the angle of incidence is known at image capture and the incoming angle of the reflected light is encoded in the grayscale of the image, the surface gradient of the object 30 can be estimated.

However, when using a uniform glass plate 90, reflected light beams passing through the plate 90 from the left and from the right are encoded at the same grayscale level, so the sign of the surface gradient is unknown. Even though a surface gradient cannot be determined using a uniform glass plate 90, using a uniform glass plate 90 does provide a more accurate measurement of the surface tilt of a specular object 30 than conventional quantization of the object surface gradient, which provides only a few discrete values of surface tilt. When inspecting printed circuit boards, the additional surface tilt information can be used to assess the quality of the solder bonds more accurately.

Figure 9:
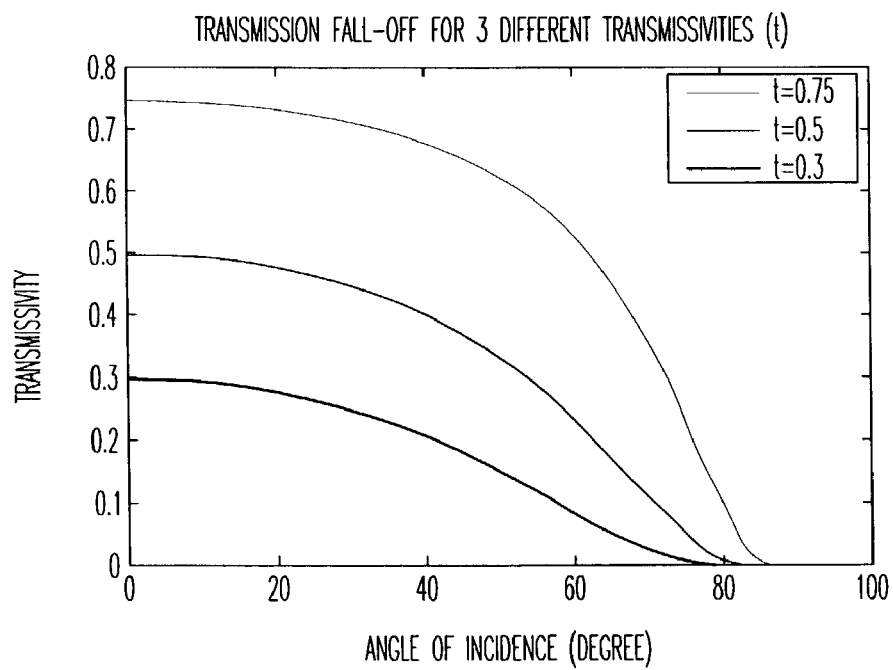
FIG. 9 is a chart illustrating of the transmissive properties of a glass filter as a function of the incoming light angle.

The percentage of light transmitted through three uniform glass filters of three different transmissivities as a function of angle of incidence are shown in FIG. 9. The higher transmissivity filter allows more light in, but gives lower contrast between low and medium angles of incidence. The lower transmissivity filter passes only 30% of the light even for angles of incidence of zero, but gives better contrast between different angles of incidence.

Turning again to FIG. 8, if the optical element 90 is a patterned glass (or plastic) filter in front of the aperture 25, instead of recording the incoming light angles, the image data can be used to determine the approximate position at which the light enters the aperture 25. The patterned filter can be a separate patterned filter located in front of the aperture 25, or a patterned coating on the lens itself For example, a patterned filter with absorption varying gradually laterally from high to low across the surface of the laterally-patterned filter can be used. For illumination that comes in from only one direction, such as in the case of collimated illumination 300, the laterally-patterned filter 90 provides a one-to-one correspondence between the measured grayscale and the object surface gradient. However, a laterally-patterned filter requires rotation of the filter for each image capture to determine the surface gradient.

In another embodiment, the optical element 90 can be a transmissive LCD screen used in front of the aperture 25 to function as a patterned filter. By using a transmissive LCD screen, the direction of the transmission gradient can be altered between image captures without requiring the use of motors and hardware to rotate the filter. However, transmissive LCD screens are more expensive than patterned filters.

Figure 11:
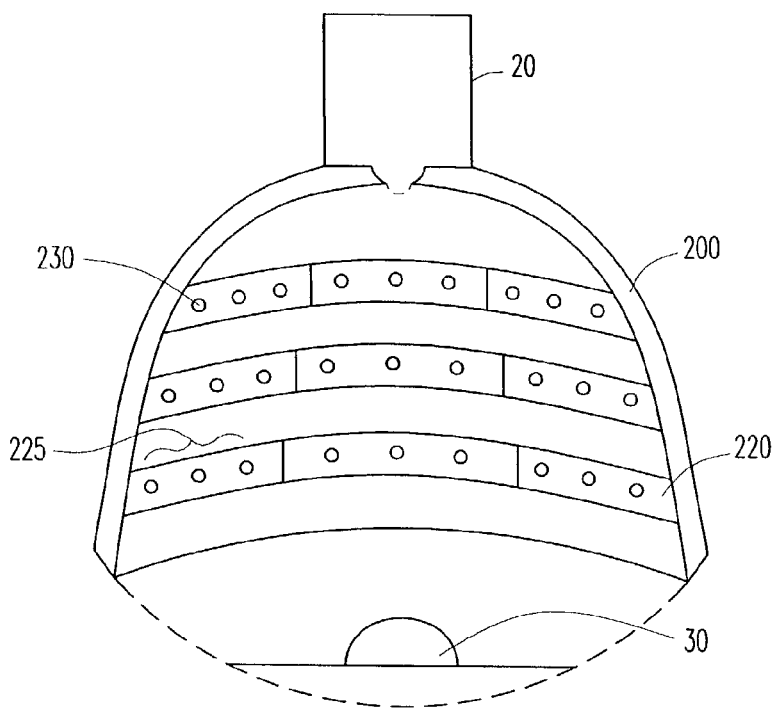
FIG. 11 is a cut-away view of a light ring having separately illuminated sections of lighting arrays, in accordance with further embodiments of the present invention.
Figure 12:
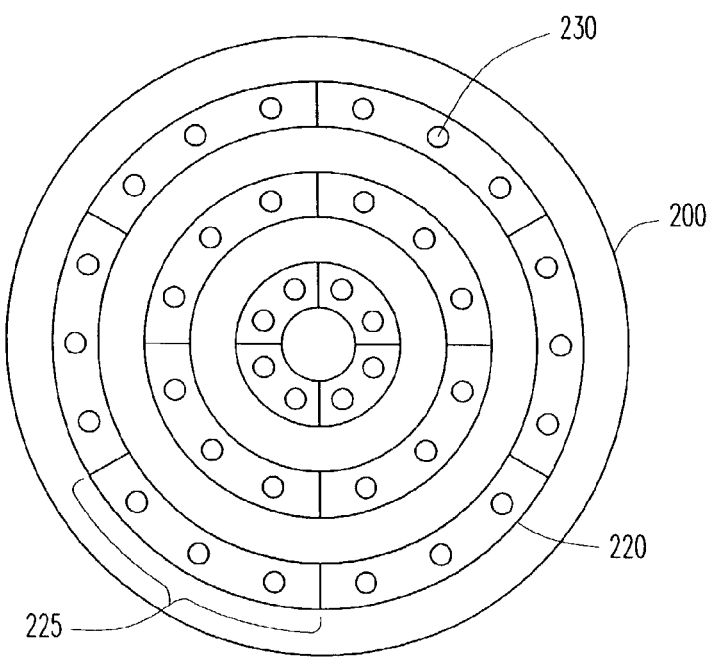
FIG. 12 is a top view of the light ring shown in FIG. 11.

In further embodiments, as shown in FIGS. 11 and 12, the illumination source can be a programmable light ring capable of being operated by the illumination control circuit 60 (shown in FIG. 1) to create sectional illumination configurations by independently controlling the sections of the light-emitting elements (e.g., LEDs) 230 that are activated to generate illumination. For example, as shown in FIGS. 11 and 12, each array 220 of light-emitting elements 230 is divided into sections 225, each having a different azimuth on the light ring 200. Each of the sections 225 can be separately controlled by the illumination control circuit to independently illuminate an object 30 with different elevations and azimuths. Thus, for each image of the object 30 taken, the object 30 is illuminated by a different section 225 of an array 220.

To improve the speed and performance of the OI system, a pre-programmed number of images can be taken, and the particular section(s) 225 used to illuminate the object 30 for each image can be pre-programmed as a pre-established illumination pattern. Thus, for each object, the OI system runs a complete image cycle, taking images under illumination from each elevation and azimuth necessary to reconstruct a three-dimensional image of the object 30. To ensure that the image data from all of the images are properly combined to reconstruct the three-dimensional image, the object 30 remains in a fixed position relative to the camera 20.

When using a sectional illumination configuration, a "photometric" stereo method can be used to reconstruct the three-dimensional image. Photometric stereo methods are typically designed for diffusely reflecting surfaces, and surface gradients are derived from several images of the same object taken with illumination from different azimuths and possibly different elevations. For surfaces that have specular and diffuse reflections, surface reconstruction is possible by taking additional images with illumination from different azimuths and possibly elevations. Additional information on photometric stereo methods can be found in Solomon, et al., "Extracting the shape and roughness of specular lobe objects using four light photometric stereo," *IEEE Transactions on Pattern Analysis and Machine Intelligence*, 18(4), pp. 449–454 (1996), and Coleman, et al., "Obtaining 3-dimensional shape of textured and specular surfaces using four-source photometry," *Computer Vision, Graphics, and Image Processing*, 18(4), pp. 309–328 (1982), both of which are hereby incorporated by reference in their entirety.

Although photometric stereo methods of obtaining the surface gradients and reconstructing three-dimensional images of textured objects are well-known in the computer vision industry, photometric stereo methods have hitherto not been applied to optical inspection of mostly specular objects (e.g., solder joints) due to the additional processing required to analyze both the specular and diffuse reflections, and therefore additional time required for each inspection. Furthermore, specular reflection data have traditionally been sufficient to produce a two-dimensional image of the surface for inspection purposes, and therefore, there has not been a need to use three-dimensional reconstruction methods, such as photometric stereo.

However, due to recent advances in the dynamic range of charge coupled device (CCD) cameras, as well as the use of a programmable light ring 200 of the type shown in FIGS. 11 and 12, sufficient diffuse reflection information can be recorded from the areas of the image with partly specular surfaces using, for example, four or more images, each captured with illumination from a different elevation, azimuth or a combination of elevation and azimuth. From the geometry of the illumination configurations (illuminated sections) and the captured images, the surface gradients of the object can be estimated, and from the estimated surface gradients, the three-dimensional surface of the object can be reconstructed using a photometric stereo. It should be understood that other reconstruction methods are possible, such as shape from shading reconstruction methods. In addition, examples of other reconstruction methods are described below in connection with FIGS. 14–19. It should further be understood that the illumination configurations can be modified depending on the surface characteristics (specular and diffuse elements) of the object to optimize the image data for reconstruction purposes.

Figure 13:
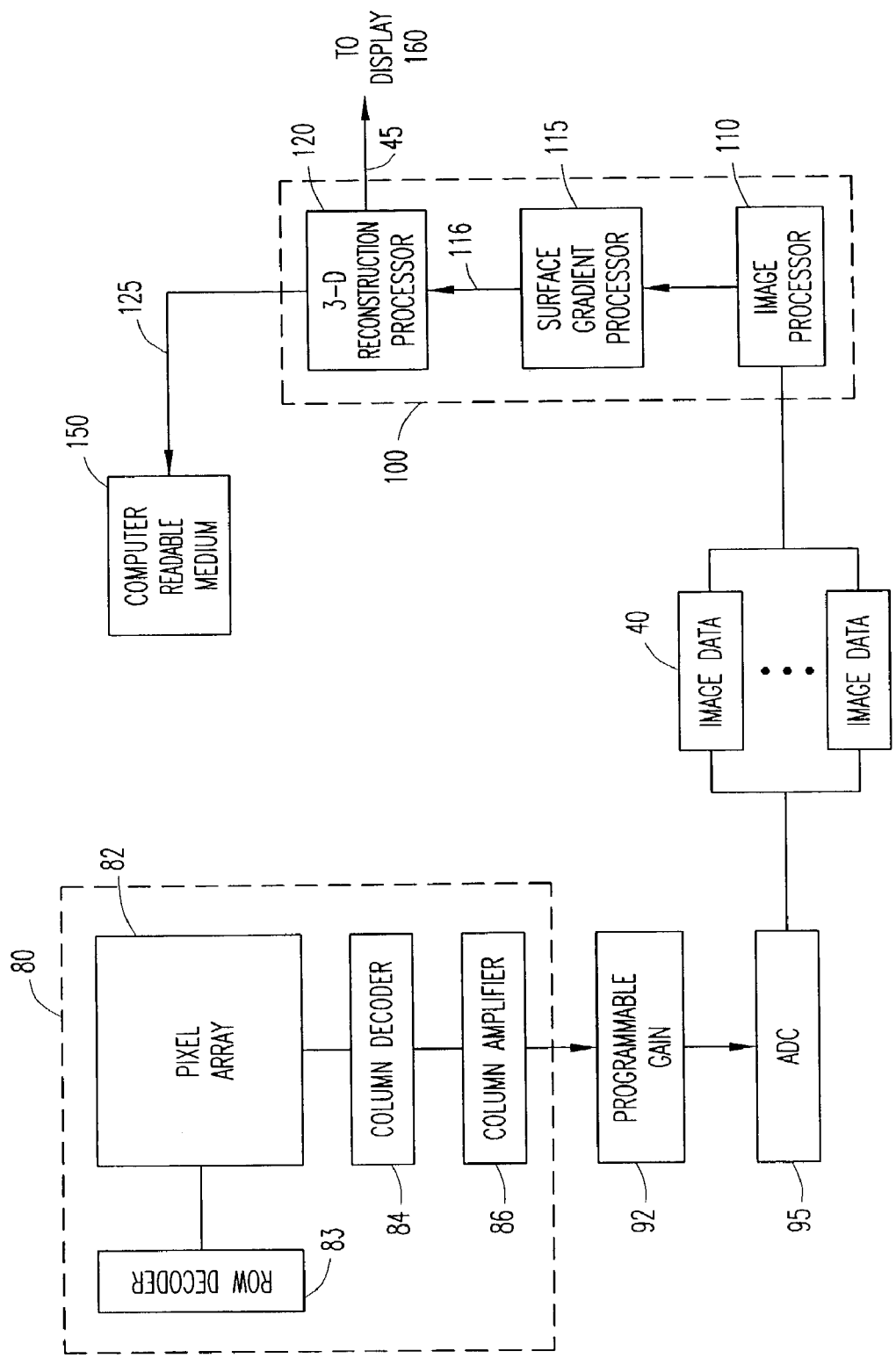
FIG. 13 is a block diagram illustrating exemplary hardware and processing components of the optical inspection system of the present invention.

FIG. 13 is a block diagram illustrating a portion of the exemplary hardware and processing components of the optical system 10 of the present invention. The optical system 10 includes the sensor 80 having a pixel array 82 for capturing an image projected thereon and for generating an analog signal representative thereof. A row decoder 83 and column decoder 84 select the rows and columns of the pixel array 82 for reading the analog signal representing the pixel values and resetting the photo detectors. A column amplifier 86 amplifies the analog signal and provides the analog signal to a programmable gain 92 before converting the analog signal to a corresponding digital signal by an analog-to-digital converter (ADC) 95.

The optical system 10 further includes the processor 100 for receiving the image data 40 including the digital signal(s) representing respective ones of one or more two-dimensional images taken under one or more illumination configurations. The processor 100 includes an image processor 110, a surface gradient processor 115 and a reconstruction processor 120. The image processor 110 is connected to receive the image data 40 representing the reflected illumination recorded at each pixel within the sensor 80 for each image and to perform any necessary pre-processing of the image data 40 prior to estimating the surface gradient and reconstructing the three-dimensional image.

For example, if a color sensor is used, the image processor 110 may need to demosaic the image. Demosaicing is a process in which missing color values for each pixel location are interpolated from neighboring pixels. There are a number of demosaicing methods known in the art today. By way of example, but not limitation, various demosaicing methods have included pixel replication, bilinear interpolation and median interpolation.

The surface gradient processor 115 takes as input the processed image data and estimates the surface gradients (surface gradient information 116) using any one of the methods described above. For example, when using illumination gradients, as described above in connection with FIGS. 2–9, the surface gradients can be estimated by determining the surface normal vectors, as described above in connection with FIG. 10. In other embodiments using sectional illumination configurations, a photometric stereo method can be used to estimate the surface gradients. However, it should be understood that any method of estimating the surface gradients can be used.

The reconstruction processor 120 is configured to receive surface gradient information 116 including the estimated surface gradients and reconstruct a three-dimensional (3-D) image 45 of the surface of the imaged object. The reconstruction processor 120 performs the 3-D surface reconstruction by finding a set of surface heights that are consistent with the surface gradient information. The surface height information 125 can be stored in the computer-readable medium 150 and/or used to provide the 3-D image 45 to the display 160.

Figure 14:
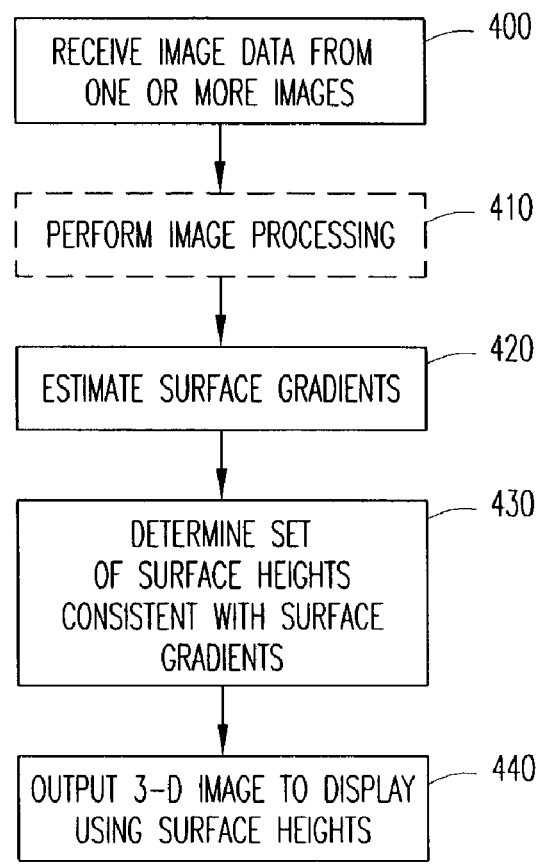
FIG. 14 is a flow chart illustrating an exemplary process for reconstructing the shape of the surface of an imaged object and displaying the reconstructed shape, in accordance with embodiments of the present invention.
Figure 15:
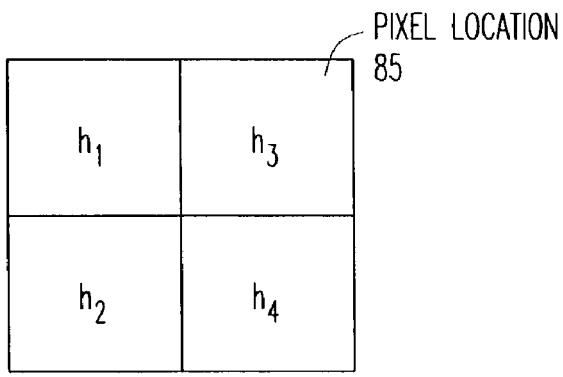
FIG. 15 illustrates a portion of a pixel array having a surface height associated with each pixel location.

In operation, as shown in FIG. 14, to perform a three-dimensional (or greater than two-dimensional) reconstruction of the surface of a specular object, one or more images of the object under different illumination configurations is taken (block 400) and the image data from the one or more images are pre-processed, if needed (block 410). From the image data and from the data representing the illumination configuration(s), surface gradients are estimated based on the known incidence angle of the light source and the angle of reflection of the light from the object surface (block 420). To reconstruct the three-dimensional object surface image, surface gradients are converted to surface heights (block 430) that can be output to a display capable of presenting to a user a three-dimensional image (or greater than 2-D image) of the object surface (block 440).

Figure 16A:
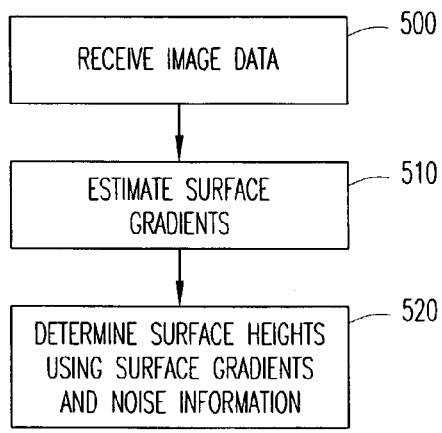
FIG. 16A is a flowchart illustrating an exemplary process for performing a noise-tolerant reconstruction process, in accordance with embodiments of the present invention.

The surface gradient information obtained in OI systems tends to be noisy and heavily quantized due to the nature of the optical inspection system and the inability to precisely control the camera noise, the amount of stray light entering the camera and the positional relationship between the illumination source, the camera and the object. Therefore, in embodiments of the present invention, a noise-tolerant reconstruction method can be used to improve noise tolerance. For example, as shown in FIG. 16A, a noise-tolerant reconstruction method uses the received image data (block 500), estimates surface gradient information from the received image data and illumination configuration(s) (block 510), as described above, and determines surface heights by adding noise information representing the noise characteristics of the optical inspection system to the surface gradient information (block 520).

Figure 16B:
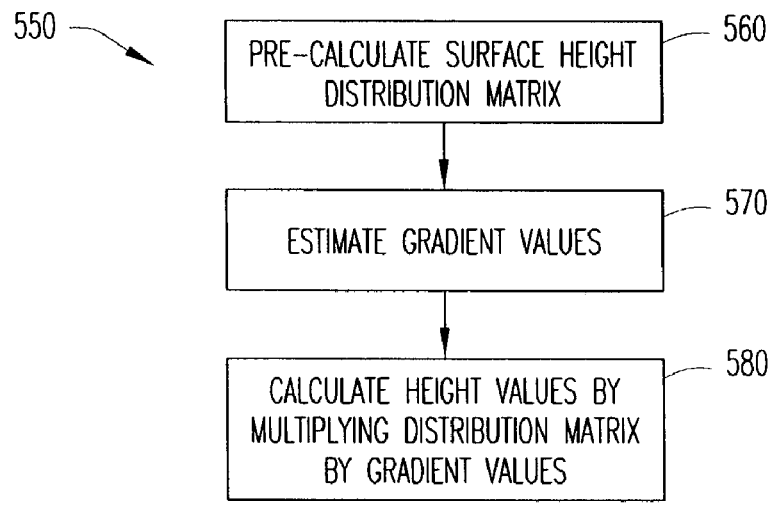
FIG. 16B is a flowchart illustrating an exemplary process for performing a bayesian noise-tolerant reconstruction process.

One example of a noise tolerant reconstruction method is shown in FIG. 16B, which uses a Bayesian reconstruction process 550 to improve noise tolerance. Since the optical inspection system uses digital image captures, the Bayes reconstruction process 550 is restricted to the discrete domain, assuming pixelated gradient maps and surface heights. If $h_{i,j}$ represents the surface height for the pixel location (i,j), with i being the horizontal (x) pixel index, and j being the vertical (y) pixel index, the gradients Dx and Dy at (i,j) are defined as:

$$Dx_{i,j} = h_{i+1,j} - h_{i,j}, \quad \text{(Equation 5)}$$

$$Dy_{i,j} = h_{i,j+1} - h_{i,j}. \quad \text{(Equation 6)}$$

Since the Dx and Dy values are linear equations involving h values, the above equations can be written in matrix form as:

$$Dx = T_x h, \quad \text{(Equation 7)}$$

$$Dy = T_y h, \quad \text{(Equation 8)}$$

where $T_x$ and $T_y$ are sparse matrices with entries of 0, 1, and −1, h is a vector of all surface height values, and $D_x$, $D_y$ are vectors of all x and y gradients. For example, for the simplified case shown in FIG. 15 of a group of four pixel locations 85, each having an associated height ($h_1$, $h_2$, $h_3$ and $h_4$), with associated gradients $dx_1$, $dx_2$, $dy_1$ and $dy_2$, where $dx_1$ is ($h_3$−$h_1$), $dx_2$ is ($h_4$−$h_2$), $dy_1$ is ($h_2$−$h_1$) and $dy_2$ is ($h_4$−$h_3$), the above gradient equation can be written as:

$$\begin{matrix} dx_1 \\ dx_2 \\ dy_1 \\ dy_2 \end{matrix} = \begin{bmatrix} -1 & 0 & 1 & 0 \\ 0 & -1 & 0 & 1 \\ -1 & 1 & 0 & 0 \\ 0 & 0 & -1 & 1 \end{bmatrix} \begin{bmatrix} h_1 \\ h_2 \\ h_3 \\ h_4 \end{bmatrix} \quad \text{(Equation 9)}$$

For gradients (dx and dy) directly measured by (or estimated from) an optical inspection system described above in connection with FIGS. 1–12, a noise term can be added to the gradient data, as follows:

$$dx = T_x h + n_x, \quad \text{(Equation 10)}$$

$$dy = T_y h + n_y, \quad \text{(Equation 11)}$$

where $n_x$ and $n_y$ are vectors of additive noise values for all pixels of the gradient images. Equations 10 and 11 can be combined into:

$$d = Th + n, \quad \text{(Equation 12)}$$

where:

$$d = \begin{pmatrix} dx \\ dy \end{pmatrix}, T = \begin{pmatrix} T_x \\ T_y \end{pmatrix}, n = \begin{pmatrix} n_x \\ n_y \end{pmatrix}. \quad \text{(Equation 13)}$$

The matrix T is fixed, and the vector d contains data (measured gradient values). To solve for the vector h, if the noise terms are assumed to be distributed as a zero-mean normal distribution $N(0,S_n)$, then a Bayes estimation method can be applied. If the height values h have a normal prior distribution $N(\mu_0,S_0)$, then the gradient values d also have a normal distribution:

$$d \sim N(T\mu_0, TS_0T' + S_n), \quad \text{(Equation 14)}$$

because the height-to-gradient transformation T is linear.

The posterior distribution of surfaces heights P(h/d) is normal with a mean $\mu_1$ of:

$$\mu_1 = J*d + (\mu_0 - J*T*\mu_0), \quad \text{(Equation 15)}$$

where $$J = S_0 T'(TS_0T' + S_n)^{-1}. \quad \text{(Equation 16)}$$

The gradient data d do not contain information about the absolute height of the object, but rather contain information about the relative heights among the pixels. Therefore, the solved height map ĥ has an arbitrary mean value. By assuming a prior distribution for h of zero mean ($\mu_0$=0), the solution can be simplified to:

$$\hat{h} = \mu_1 = J*d. \quad \text{(Equation 17)}$$

For fixed $S_0$ and $S_n$, the gradient-to-height matrix J does not depend on the data, and, as shown in FIG. 16B, can be pre-calculated and stored in memory (block 560). Once the gradient values are estimated (block 570), the height estimate then becomes a simple multiplication between a matrix and a vector (block 580). Therefore, for moderate-sized images with identical noise distribution for all gradient values, the Bayes process 550 can be implemented easily and can run quickly.

The Bayes process 550 also allows different error distributions for different pixels, making it possible to obtain an acceptable height reconstruction even when some of the pixels have missing gradient information, or unreliable gradients relative to other pixels. This can be useful for systems that cannot capture all possible gradient levels, such as an optical inspection system that can only capture a limited range of surface angles. The noise information can be incorporated into the estimation process in several ways. For example, the noise information can be included in the noise term $S_n$ or in the prior mean and covariance matrix terms $\mu_0$ and $S_0$.

For example, in an optical inspection system that can only capture specular reflections from surfaces having a maximum surface gradient of 23 degrees and diffuse reflections from surfaces having a maximum surface gradient of 45 degrees, for steep surfaces with surface gradients greater than 45 degrees, a confidence map can be used in conjunction with the Bayes process 550 to apply a best fit of the object surface to the image data. Prior to applying the Bayes reconstruction process 550, a confidence map can be created based on the estimated surface gradients. Within the confidence map, a weight or value is assigned to each pixel location indicating the confidence or reliability of the surface gradient at that pixel location. A smaller error distribution is applied to pixel locations having high confidence values, while a larger error distribution is applied to pixel locations having low confidence values. This confidence map can be used to set the prior covariance matrix in the Bayes height reconstruction formulation. In further embodiments, computer-aided design (CAD) data that provides information concerning the design specifications (e.g., shape or size) of the object can be used to supplement the image data by providing a more specific prior mean matrix $\mu_0$.

Figure 18:
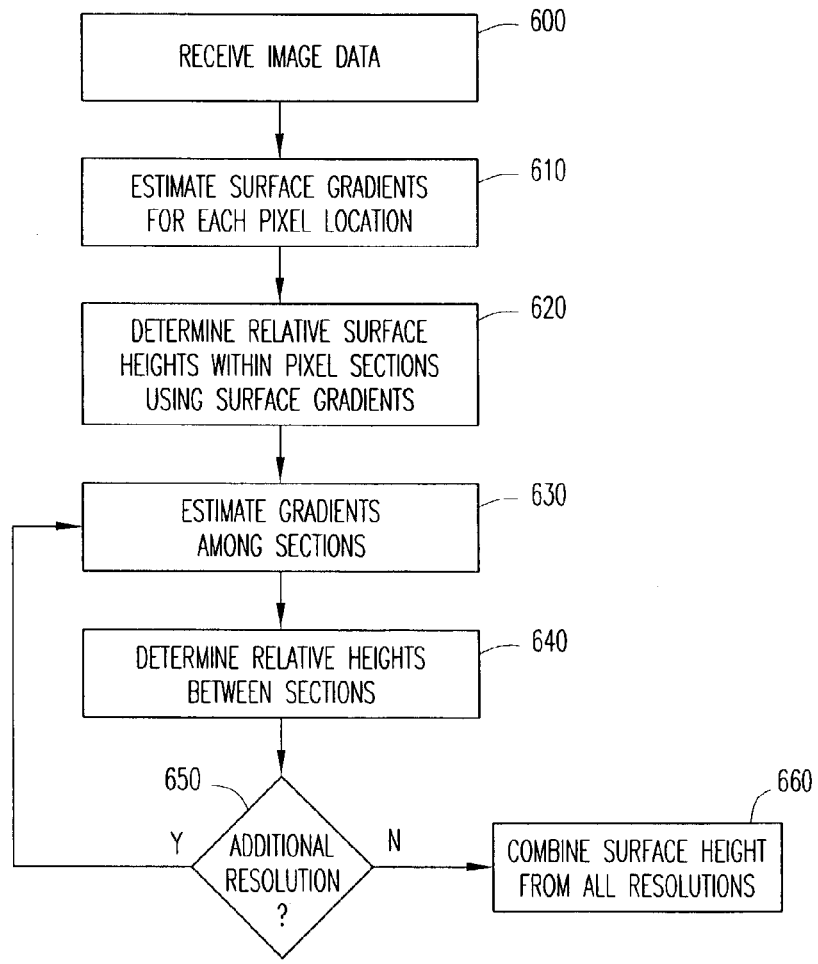
FIG. 18 is a flowchart illustrating an exemplary process for performing a multi-resolution reconstruction process, in accordance with embodiments of the present invention.

In other embodiments, for large images (with a large number of pixel values), a multi-resolution reconstruction method that processes the image data in small components (e.g., pixel values from small sections of pixel locations) can be used to achieve global gradient consistency efficiently without requiring iterative searches, thereby improving the speed of calculations. As shown in FIG. 18, in a multi-resolution process, the received image data (block 600) are used to estimate the surface gradient for each pixel location (block 610), as described above. Thereafter, the relative surface heights within each of the sections of pixel locations are determined using the surface gradient information for the pixel locations in the section (block 620). For each level of resolution representing the size of the pixel sections, the surface gradients among the sections are estimated (block 630) and the relative surface heights among the sections are determined from the estimated surface gradients for the sections (block 640). Once the needed number of resolutions has been achieved depending on the image size (block 650), the surface heights determined with each resolution are combined to produce the final surface height information for the object (block 660).

Figure 19A:
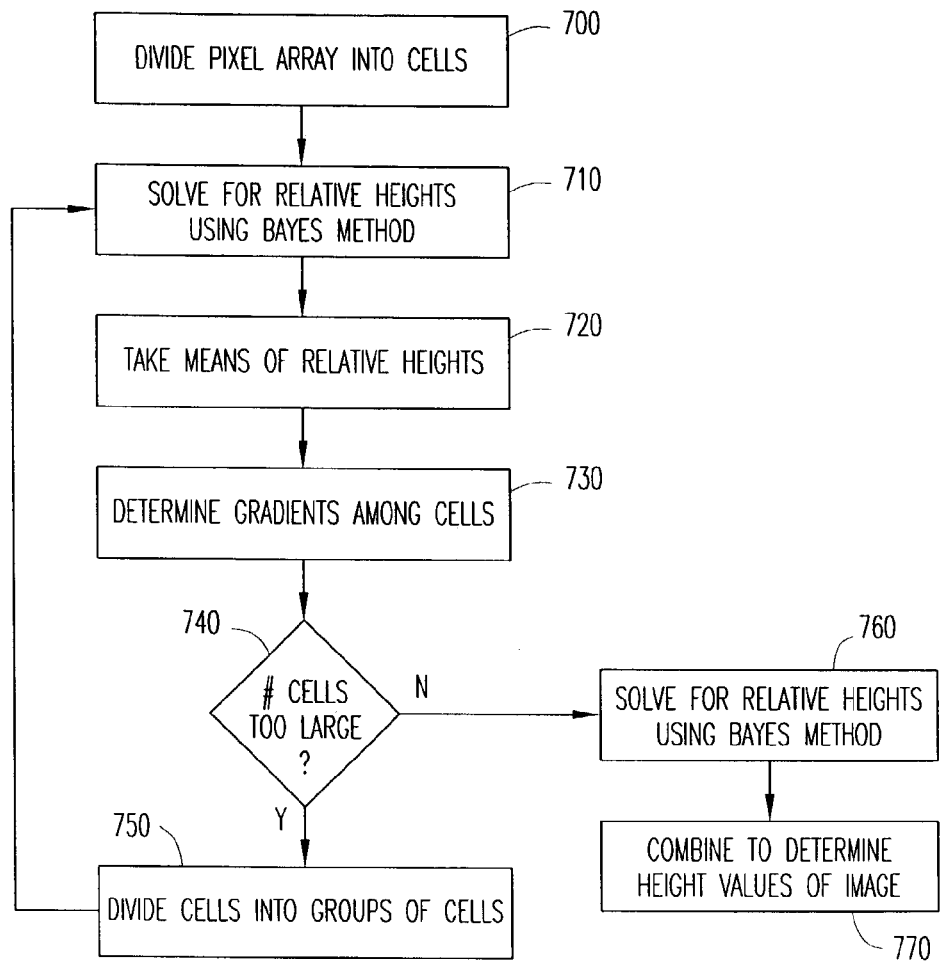
FIG. 19A is a flowchart illustrating an exemplary process for performing a multi-resolution bayesian reconstruction process.

For example, referring now to FIG. 19A, the multi-resolution reconstruction method can be used with the Bayesian process described above with reference to FIG. 16B. For large images, the matrix T is large, and the matrix inversion in Equation 16 becomes difficult. Even if the inversion is performed off-line, the resulting matrix T may still be too large to process. For example, for an image of size 100×100 pixels, the size of the matrix T will be 19800×19800, and thus matrix T will be very cumbersome to store and access.

Figure 17:
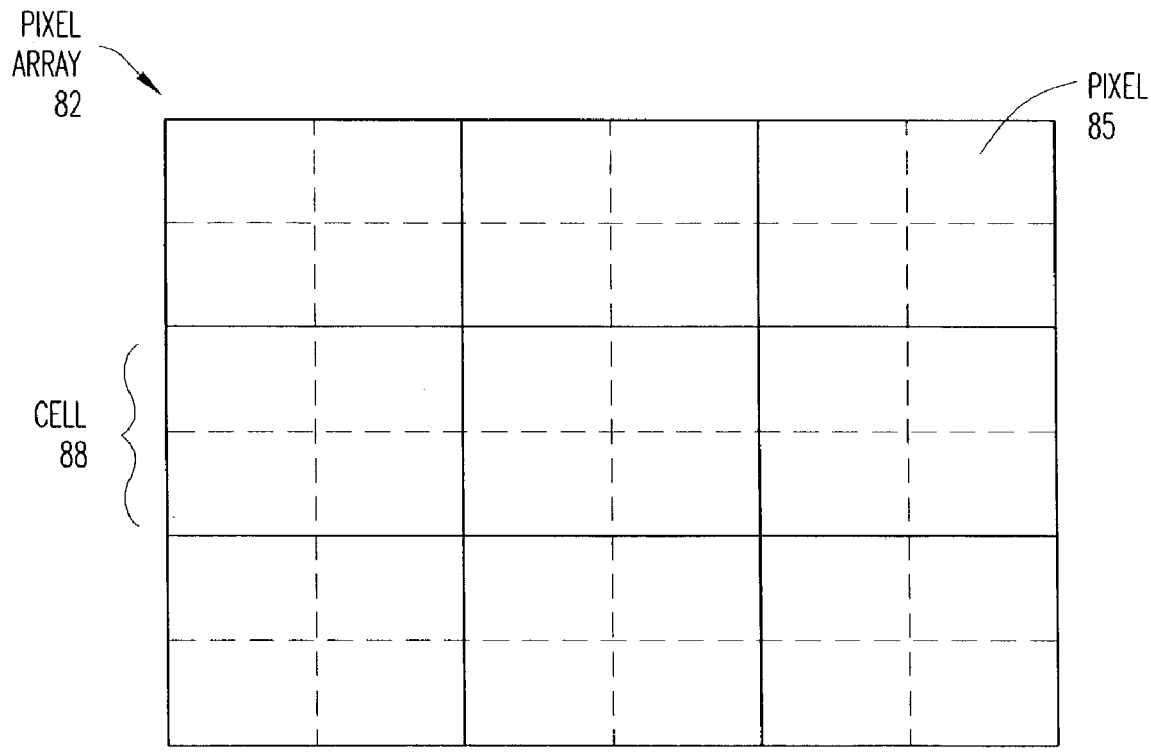
FIG. 17 illustrates a portion of a pixel array divided into cells of multiple pixels.

Therefore, to reduce the size of the matrix T, the pixels can be processed in only small areas at a time, while still achieving global gradient consistency by estimating the height values at multiple resolutions. As shown in FIG. 17, initially, the object images can be partitioned into individual cells 88 of m×m pixels 85 of the pixel array 82, where m is an integer greater than or equal to two.

Turning now to FIG. 19A, once the pixel array has been divided into larger "pixels" (cells) (block 700), if the estimated heights of pixel (i,j) in cell (p,q) are represented by $\hat{h}_{i,j,p,q}$, the relative heights within each cell can be solved according to the Bayes reconstruction method outlined in FIG. 16B (block 710), with mean height of each cell normalized to 0, so that:

$$\sum_{i=1}^{m}\sum_{j=1}^{m} \hat{h}_{i,j,p,q} = 0. \qquad \text{(Equation 18)}$$

Each cell is then treated as one pixel having a height equal to the mean of the m×m individual heights (block 720). The gradients among the cells are easily computed from the original gradient images as (block 730):

$$\begin{aligned}
dx_{p,q} &= \sum_{j=1}^{m}\sum_{i=1}^{m} h_{i,j,p+1,q} - \sum_{j=1}^{m}\sum_{i=1}^{m} h_{i,j,p,q} \\
&= \sum_{j=1}^{m}\sum_{i=1}^{m} (h_{i,j,p+1,q} - h_{i,j,p,q}) \\
&= \sum_{j=1}^{m}\sum_{i=1}^{m}\sum_{k=0}^{m} (h_{i+k+1,j,p,q} - h_{i+k,j,p,q}) \\
&= \sum_{j=1}^{m}\sum_{i=1}^{m}\sum_{k=0}^{m} dx_{i+k,j,p,q}, \\
dy_{p,q} &= \sum_{j=1}^{m}\sum_{i=1}^{m} h_{i,j,p,q+1} - \sum_{j=1}^{m}\sum_{i=1}^{m} h_{i,j,p,q} \\
&= \sum_{j=1}^{m}\sum_{i=1}^{m}\sum_{k=0}^{m} dy_{i,j+k,p,q}
\end{aligned} \qquad \text{(Equations 19)}$$

After obtaining the gradients among the cells, the relative heights among the cells can be solved to obtain the estimated height values $\hat{h}_{p,q}$ (block 760). However, if the number of cells is still too large for a direct solution using the Bayes reconstruction process outlined in FIG. 16B (block 740), the cells can be combined into groups of n×n larger cells (block 750), and blocks 710–730 can be recursively run until the height can be solved directly.

Once the estimated height values $\hat{h}_{p,q}$ for the cells have been calculated (block 760), all of the multi-resolution solutions can be combined to obtain the final height map as follows (block 770):

$$h_{i,j,p,q} = \hat{h}_{i,j,p,q} + \hat{h}_{p,q}, \qquad \text{(Equation 20)}$$

where $\hat{h}_{p,q}$ itself may be a combination of height estimates from several resolution levels.

Figure 19B:
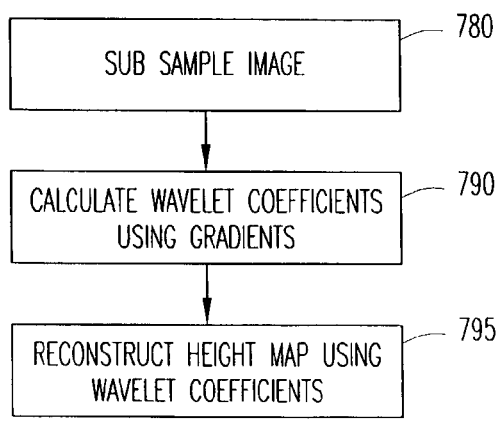
FIG. 19B is a flowchart illustrating an exemplary process for performing a multi-resolution wavelet reconstruction process.

In FIG. 19A, a block pyramid decomposition process was used for the multi-resolution processing. However, it should be understood that other ways of performing multi-resolution decomposition can be used as well. For example, as shown in FIG. 19B, a wavelet decomposition process can be used on the gradient images, and the different resolution levels can be solved for separately before being combined into the final solution. The preferred wavelet decomposition has a high frequency decomposition filter $f_{high}$ that can be expressed as a convolution of a filter $f_1$ and the difference filter (−1 1):

$$f_{high} = (-1\ 1)f_1. \qquad \text{(Equation 21)}$$

There are many commonly-used wavelet filters (e.g., the Daubechies filters) that can be expressed using Equation 18. For a height image h, the first level of wavelet decompositions can be calculated as described below, which results in 4 images: (1) the high frequency image $h_{22}$, (2) the low frequency image $h_{11}$, (3) the horizontally high frequency image $h_{21}$, and (4) the vertically high frequency image $h_{12}$. If S represents the operation of subsampling an image by a factor of two on each dimension (block 780), then by combining the wavelet decomposition operations with Equations 10, 11 and 21, the images are as follows:

$$\begin{aligned}
h_{11} &= S(h \otimes_x f_{low} \otimes_y f_{low}), \\
h_{12} &= S(h \otimes_y f_{high} \otimes_x f_{low}) \\
&= S(h \otimes_y (-1\ 1) \otimes_y f_1 \otimes_x f_{low}) \\
&= S(Dy \otimes_y f_1 \otimes_x f_{low}), \\
h_{21} &= S(h \otimes_x f_{high} \otimes_y f_{low}) \\
&= S(h \otimes_x (-1\ 1) \otimes_x f_1 \otimes_y f_{low}) \\
&= S(Dx \otimes_x f_1 \otimes_y f_{low}), \\
h_{22} &= S(h \otimes_x f_{high} \otimes_y f_{high}) \\
&= S(Dx \otimes_x f_1 \otimes_y f_{high}) \\
&= S(Dy \otimes_y f_1 \otimes_x f_{high}).
\end{aligned} \qquad \text{(Equations 22)}$$

The wavelet coefficients $h_{12}$, $h_{21}$, and $h_{22}$ can all be estimated (block 790) by substituting dx and dy for Dx and Dy in the above Equations 22. It should be noted that $h_{22}$ can be calculated from either dx or dy. For example, an average of dx and dy can be used to calculate $h_{22}$, but it should be understood that other combinations of dx and dy can be used as well. The wavelet terms then become:

$$\hat{h}_{12} = S(dy_y f_{1x} f_{low}), \qquad \text{(Equation 23)}$$

$$\hat{h}_{21} = S(dx_x f_{1y} f_{low}), \qquad \text{(Equation 24)}$$

$$\hat{h}_{22} = (S(dx_x f_{1y} f_{high}) + S(dy_y f_{1x} f_{high}))/2. \qquad \text{(Equation 25)}$$

However, the wavelet term $h_{11}$ cannot be directly derived from dx and dy. However, $h_{11}$ can be treated as a height map by itself, and the gradients of $h_{11}$, denoted $dx_{11}$ and $dy_{11}$, can be estimated from the data dx and dy. From Equations 10 and 11 above:

$$\begin{aligned}
Dx_{11} &= h_{11} \otimes_x (-1\ 1) \\
&= S(h \otimes_x f_{low} \otimes_y f_{low}) \otimes_x (-1\ 1) \\
&= S(h \otimes_x f_{low} \otimes_y f_{low}) \otimes_x (-1\ 0\ 1)) \\
&= S(h \otimes_x (-1\ 1) \otimes_x (1\ 1) \otimes_x f_{low} \otimes_y f_{low}) \\
&= S(Dx \otimes_x (1\ 1) \otimes_x f_{low} \otimes_y f_{low}), \\
Dy_{11} &= S(Dy \otimes_y (1\ 1) \otimes_y f_{low} \otimes_x f_{low}).
\end{aligned} \qquad \text{(Equation 26)}$$

Therefore, gradients for the wavelet term $h_{11}$ can be estimated as:

$$dx_{11} = S(dx_x (1\ 1)_x f_{low_y} f_{low}), \qquad \text{(Equation 27)}$$

$$dy_{11} = S(dy_y (1\ 1)_y f_{low_x} f_{low}). \qquad \text{(Equation 28)}$$

With known gradients $dx_{11}$ and $dy_{11}$, the elements in $h_{11}$ can now be solved recursively using either the block pyramid method or the wavelet pyramid method. Once all the wavelet coefficients $h_{11}$, $h_{12}$, $h_{21}$, and $h_{22}$ have been solved for, the wavelet coefficients can be reconstructed to the full height map using standard wavelet reconstruction procedures (block 795).

In the wavelet pyramid shown in FIG. 19B, the Bayes process was not used as described in FIG. 16B to perform the height estimates, and thus the noise tolerance is not as good as the block pyramid case. However, the wavelet pyramid calculation can be done faster than the Bayes calculation, and therefore the wavelet pyramid method can be useful for situations where the data noise is known to be low.

In all Bayes processes (e.g., FIGS. 16B and 19A), when transformations are applied on the gradient images, the noise terms among the transformed values will have different covariance than the original covariance for the gradients. Therefore the covariance matrix $S_n$ for the noise term n should go through appropriate transformations as well if a Bayes height estimation is used. The Bayes height estimation method works optimally when the noise covariance is specified properly such that the level of uncertainty in the gradient data can be properly reflected in the posterior distribution (mean and covariance) of the height, resulting in more reliable height estimates.

Figure 20:
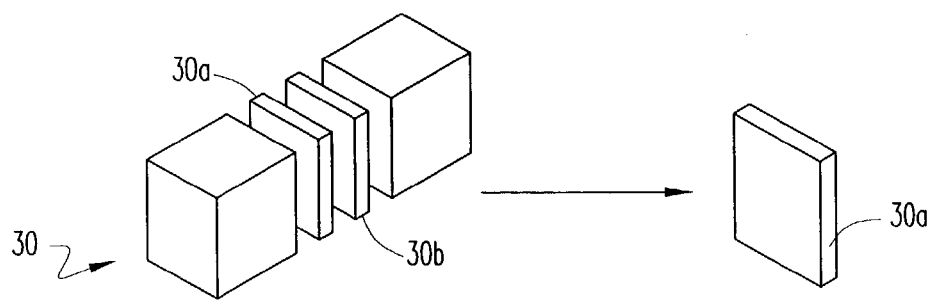
FIG. 20 is a pictorial representation of 2.5D images of an object.

In other embodiments, instead of reconstructing a complete three-dimensional image, to reduce processing time, a "2.5-D" reconstruction of the image can be performed, in which a slice of the three-dimensional image is reconstructed using select data points. For example, as shown in FIG. 20, the surface of an object 30 can be divided into slices 30a and 30b, and the shape of the surface of a select one of the slices 30a can be reconstructed from the image data. To reconstruct a selected slice 30a of the image, the image data from the pixel locations within the selected slice 30a are used to estimate the surface gradients of the slice 30a and a reconstruction method (e.g., the Bayes reconstruction process described above in connection with FIGS. 16B and 19A) can be applied to the estimated surface gradients. From the reconstructed slice 30a of the image, various object features can be estimated, such as surface height. In the optical inspection system, the estimated object features can be compared to the design specifications for the object to determine whether there are any defects in the object. It should be understood that the term "slice" as it is used to define a "2.5-D" image refers to any portion of the 3-D image, and can be of any shape or size.

Figure 21:
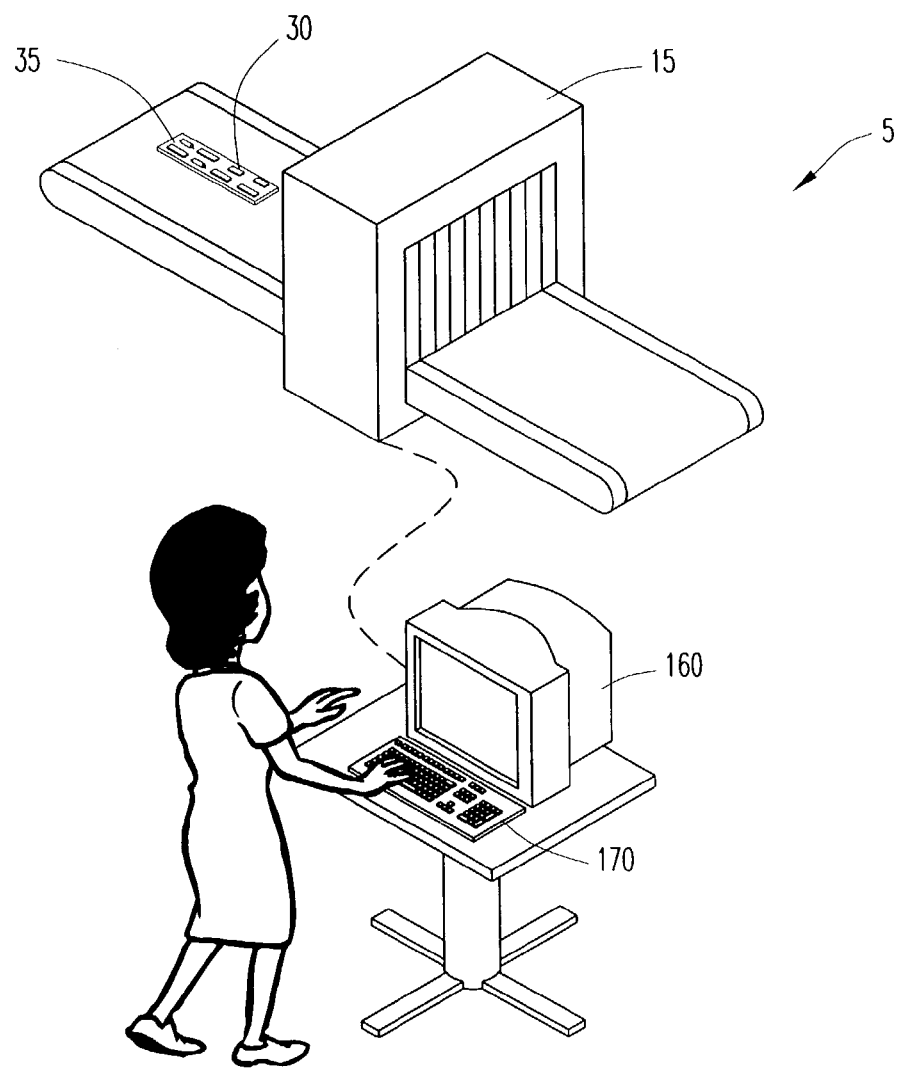
FIG. 21 is a pictorial representation of an optical inspection system having a three-dimensional display, in accordance with embodiments of the present invention.

Referring now to FIG. 21, printed circuit board (PCB) inspection systems 5 typically include a machine vision apparatus 15 that images a printed circuit board (PCB) 35 to inspect objects 30 (e.g., solder joints and/or components) on the PCB 35 to determine whether one or more of the objects 30 is defective. The OI system 10 of FIG. 10 forms aspects of the PCB system 5. In many PCB inspection systems 5, only the images of the joint/components that were classified as defective by the apparatus 15 are presented to a user. Due to the large number of joints/components on each PCB 35, it is usually not feasible for the user to inspect all of the joints/components.

To enhance the ability of the user to identify defective joints/components, the image obtained by the apparatus 15 can be displayed in greater than two dimensions on a display 160. The display 160 can be a three-dimensional display, such as a sharp screen, 3-D ball, user glasses (e.g., 3-D glasses or virtual reality glasses), or other type of three-dimensional display. In other embodiments, the display 160 can be a "rocking" two-dimensional display that uses a rocking motion of the image 45 to rotate the image 45 to create a three-dimensional image in the mind of the observer. The rocking can be automatic or controlled by a user. In further embodiments, the display 160 can be a two-dimensional projection of the 3-D image that allows the user to rotate the angle of viewing. The viewing angle can be manipulated through a user interface 170, such as a keyboard (as shown), joystick, virtual reality interface or other type of control. In addition, the user interface 170 can enable the user to control the information presented on the display 160. For example, through the user interface 170, the user can select only certain portions of the image to be displayed in 3-D.

Figure 22:
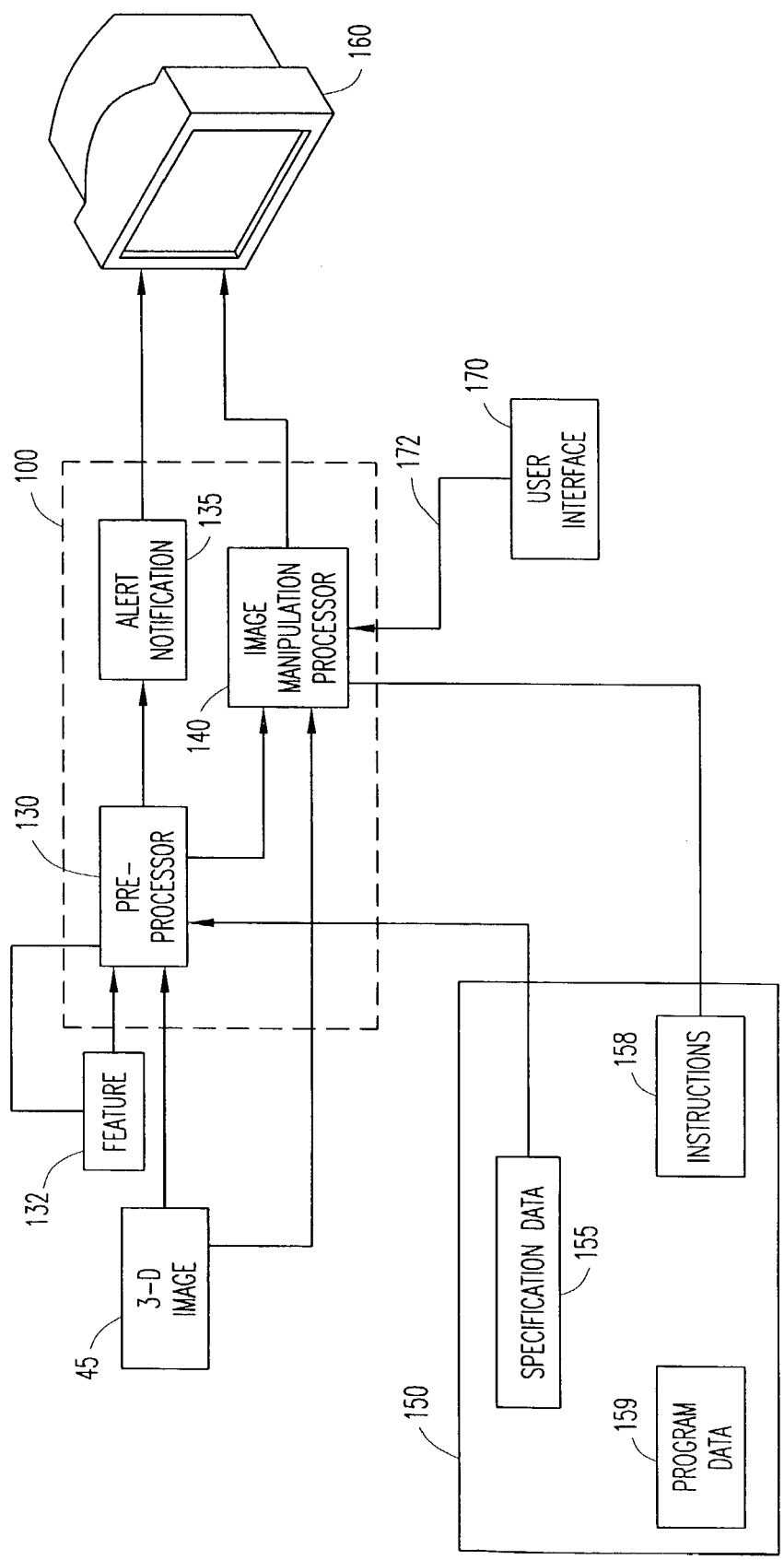
FIG. 22 is a block diagram illustrating the hardware and processing components of a three-dimensional display optical inspection system.

Turning now to FIG. 22, upon reconstruction of a greater than two-dimensional (e.g., 3-D) image of the object, the processor 100 can perform additional processing of the greater than two-dimensional (e.g., 3-D) image 45 prior to or during display of the 3-D image 45 on a display 160. For example, the processor 100 can include a pre-processor 130 that estimates various object features 132 and performs a comparison of the estimated object features 132 to pre-defined object specification data 155 stored in the computer-readable medium 150. The specification data 155 can include a threshold or range for the object features, outside of which the object may be considered defective. If the results of the comparison indicate that the object may be defective, the pre-processor 130 instructs an alert notification processor 135 to create and output an alert notification indicator to alert the user that an object may be defective and visual inspection by the user is required. The alert notification indicator can be a visual indicator on the display 160 and/or a sound indicator provided through a sound card or other sound device connected to the display 160.

In other embodiments, the pre-processor 130 uses features 132 identified from either the complete reconstructed 3-D image 45, a portion of the 3-D image (e.g., a 2.5-D image) or other image data that can be used to reconstruct the 3-D image to compare with the specification data 155 to automatically classify the object as defective or acceptable. For example, the pre-processor 130 can identify the surface height, volume, width or other feature 132 from the image data provided to the pre-processor 130, and compare the feature 132 with the specification data 155 for the object to automatically distinguish between good and bad parts. By automatically classifying objects, the amount of manual labor required to inspect PCBs can be reduced or eliminated. For example, if the comparison results are close, 3-D images 45 for those objects can be displayed. Otherwise, no image would need to be displayed. In other embodiments, the 3-D image 45 and/or results of the comparison can be used as program data 159 to train or program the pre-processor 130 to automatically classify objects based on new 3-D images or image data.

An image manipulation processor 140 can be connected to receive the 3-D image 45 from the pre-processor 130 to enhance the 3-D image 45 prior to display of the 3-D image 45 to the user. For example, the image manipulation processor 140 can isolate certain areas of the object surface that are of interest and highlight those areas or otherwise provide visual clues to the user of the problem areas on the object surface. The enhancements performed on the image can be pre-defined by the user or manufacturer and performed on all displayed 3-D images 45. For example, computer executable instructions 158 defining the enhancements can be stored in software modules in the computer-readable medium 150 and loaded and executed by the image manipulation processor.

In addition, during the display of the 3-D image 45 to the user, the image manipulation processor 140 can be connected to receive image manipulation instructions 172 from the user interface 170 based on an image manipulation input provided by the user to the user interface 170 to alter the 3-D image 45 displayed. For example, the image manipulation processor 140 can receive instructions 172 to display certain areas of the object surface or rotate the angle of viewing of the object surface.

Figure 23:
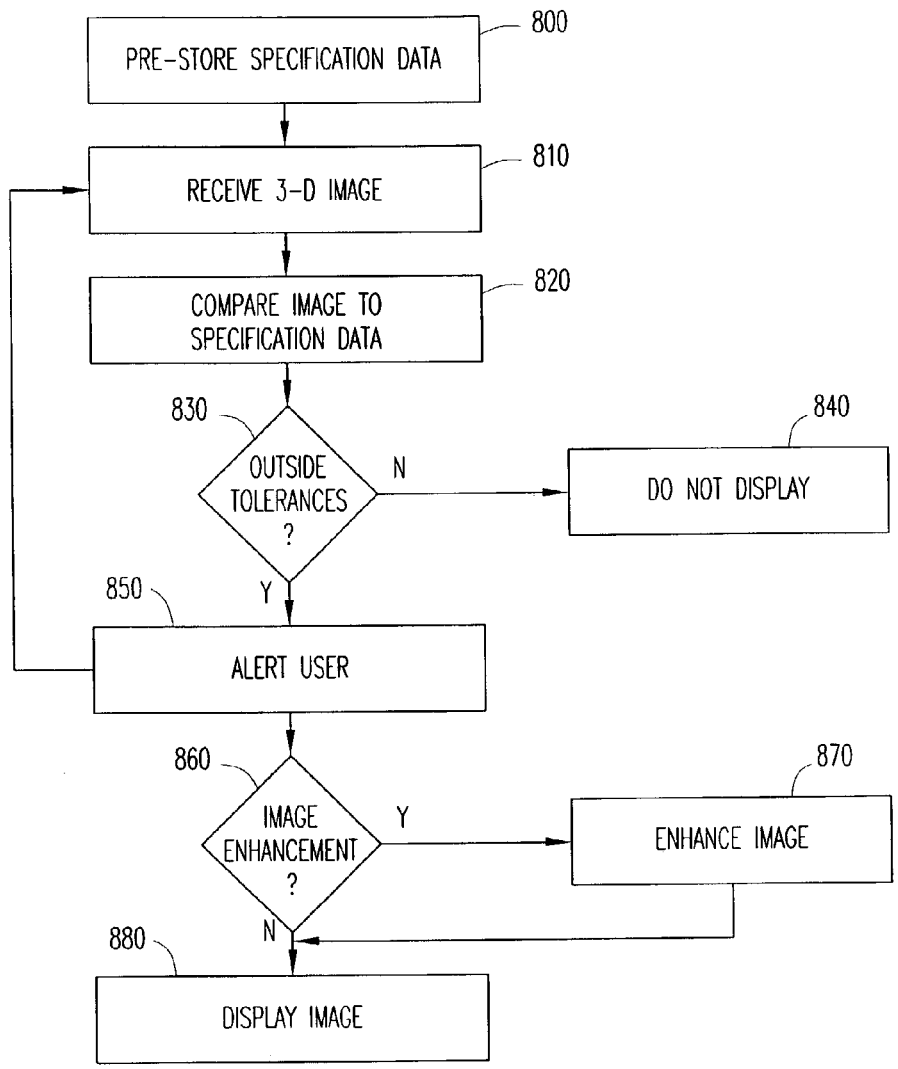
FIG. 23 is a flowchart illustrating an exemplary process for displaying three-dimensional images of an object, in accordance with embodiments of the present invention.

In operation, as shown in FIG. 23, to provide the user with 3-D views of only those objects that may be defective, specification data on the objects can be pre-stored (block 800), so that upon reconstruction of the 3-D image of the object (block 810), the specification data can be compared to object features estimated from the 3-D image (block 820) to determine if the estimated object features are outside of tolerances for the object (block 830). If the comparison indicates that the object features are within tolerances (e.g., the object is not defective) (block 830), the 3-D image is not displayed to the user (block 840). However, if the comparison indicates that the object features are outside of tolerances (block 830), the user is alerted (block 850). If there are any image enhancements that need to be performed on the 3-D image (block 860), those image enhancements are performed (block 870) prior to display of the 3-D image to the user (block 880).

Figure 24:
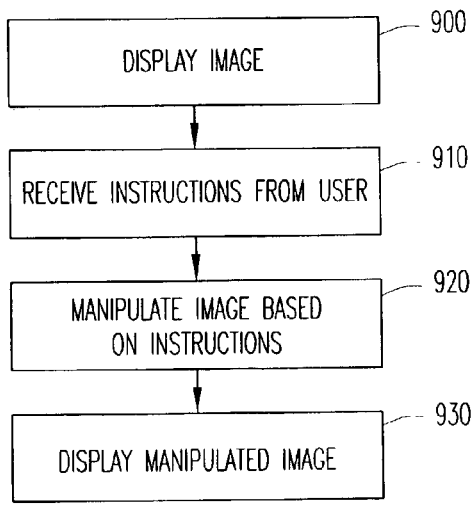
FIG. 24 is a flowchart illustrating an exemplary process for manipulating the displayed three-dimensional image of an object, in accordance with embodiments of the present invention.

Referring now to FIG. 24, once the 3-D image is displayed to the user (block 900), the user can manipulate the 3-D image by providing image manipulation instructions to the OI system through a user interface (block 910). The OI system is capable of manipulating the 3-D image in virtually any manner possible based on the user manipulation instructions (block 920). Once the 3-D image has been manipulated in accordance with the user's instructions, the manipulated 3-D image can be displayed to the user (block 930), and further manipulations can be performed until the user is able to determine whether the object is defective.

As will be recognized by those skilled in the art, the innovative concepts described in the present application can be modified and varied over a wide range of applications. Accordingly, the scope of patented subject matter should not be limited to any of the specific exemplary teachings discussed, but is instead defined by the following claims.

We claim:

1. A printed circuit board inspection system for inspecting objects on a printed circuit board, comprising:
a display operable to display a greater-than two dimensional image of the shape of the surface of an object resident on the printed circuit board, the image being displayed in at least two dimensions and being generated based on optical imaging of the object under different illumination configurations; and
a processor operable to generate the greater-than two dimensional image and provide the greater-than two dimensional image to said display; wherein said processor includes a pre-processor operable to estimate at least one object feature from the greater-than two dimensional image and perform a comparison of the object feature to specification data associated with the object.

2. The printed circuit board inspection system of claim 1, wherein said processor further comprises:
an image manipulation processor operable to receive the image and alter the displayed image.

3. The printed circuit board inspection system of claim 2, further comprising:
a computer readable medium having computer executable instructions therein for enhancing the image, said image manipulation processor being connected to said computer readable medium to retrieve the computer executable instructions, enhance the image according to the computer-executable instructions and provide the enhanced image to said display.

4. The printed circuit board inspection system of claim 2, further comprising:
a user interface operable to receive image manipulation input from a user and to provide to said image manipulation processor image manipulation instructions based on the image manipulation input, said image manipulation processor being operable to manipulate the image in response to the image manipulation instructions and to provide the manipulated image to said display.

5. The printed circuit board inspection system of claim 4, wherein the image manipulation instructions operate to alter the viewing angle of the image.

6. The printed circuit board inspection system of claim 1, further comprising:
a computer-readable medium having the specification data stored therein, said pre-processor being connected to said computer-readable medium to retrieve the specification data.

7. The printed circuit board inspection system of claim 1, wherein said processor further comprises:
an alert notification processor operable to transmit to a device associated with said display an alert notification indictor based on the results of the comparison.

8. The printed circuit board inspection system of claim 1, wherein said display is a three-dimensional display.

9. The printed circuit board inspection system of claim 1, wherein said display is a two-dimensional display.

10. A method for displaying a greater-than-two dimensional image of an object resident on a printed circuit board during an optical inspection process, comprising:
receiving an image of the shape of the surface of an object resident on the printed circuit board, the image being in greater than two dimensions and generated based on optical imaging of the object under different illumination configurations;
estimating at least one object feature of the image;
performing a comparison of the object feature to specification data associated with the object; and
displaying the image in at least two dimensions on a display.

11. The method of claim 10, wherein said displaying comprises:
storing computer-executable instructions for enhancing the image;
enhancing the image according to the computer-executable instructions; and
providing the enhanced image to the display.

12. The method of claim 10, further comprising:
receiving image manipulation instructions for altering the displayed image;
manipulating the image in response to the image manipulation instructions; and
providing the manipulated image to display.

13. The method of claim 12, wherein said manipulating comprises:
altering the viewing angle of the image.

14. The method of claim 13, wherein said altering comprises:
rotating the image displayed on a two-dimensional display to convey a three-dimensional representation of the shape of the surface of the object.

15. The method of claim 10, further comprising:
storing the specification data.

16. The method of claim 15, further comprising:
transmitting to a device associated with the display an alert notification indicator based on the results of the comparison; and
providing the image to said display upon transmission of the alert notification indictor.

17. The method of claim 10, wherein said displaying comprises:
displaying the image to a user for the inspection of the object.

18. A method for selectively displaying a greater than two-dimensional image of an object during an optical inspection process, comprising;
storing specification data associated with the object;
receiving an image of the shape of the surface of an object resident on the printed circuit board, the image being in greater than two dimensions and generated based on optical imaging of the object under different illumination configurations;
estimating at least one object feature from the image;
performing a comparison of the specification data and the object feature; and
based on the results of the comparison selectively displaying the object image in at least two dimensions on a display.

19. The method of claim 18, in which said displaying comprises:
based on the results of the comparison, transmitting an alert notification indictor to a device associated with the display; and
providing the image to said display upon transmission of the alert notification indicator.

20. A method for manipulating a greater-than-two dimensional image of an object during an optical process, comprising:
receiving an image of the shape of the surface of an object resident on the printed circuit board, the image being in greater than two dimensions and generated based on optical imaging of the object under different illumination configurations;
receiving instructions for altering the displayed image;
manipulating the image in response to the instructions; and
providing the manipulated image to an at least two-dimensional display.

21. The method of claim 20, wherein said receiving instructions comprises:
storing computer-executable instructions for enhancing the image;
enhancing the viewing angle of the image according to the computer-executable instructions; and
providing the enhanced image to the display.

* * * * *

UNITED STATES PATENT AND TRADEMARK OFFICE
CERTIFICATE OF CORRECTION

| | |
|---|---|
| PATENT NO. | : 7,171,037 B2 |
| APPLICATION NO. | : 10/393413 |
| DATED | : January 30, 2007 |
| INVENTOR(S) | : Mahon et al. |

It is certified that error appears in the above-identified patent and that said Letters Patent is hereby corrected as shown below:

In column 22, line 3, in Claim 3, after "a" delete "computer readable" and insert -- computer-readable --, therefor.

In column 22, line 3, in Claim 3, after "having" delete "computer executable" and insert -- computer-executable --, therefor.

In column 22, line 6, in Claim 3, before "medium" delete "computer readable" and insert -- computer-readable --, therefor.

In column 22, lines 6-7, in Claim 3, after "the" delete "computer executable" and insert -- computer-executable --, therefor.

In column 22, line 33, in Claim 7, delete "indictor" and insert -- indicator --, therefor.

In column 22, line 64, in Claim 12, after "to" insert -- the --.

In column 23, line 13, in Claim 16, delete "indictor" and insert -- indicator --, therefor.

In column 23, line 20, in Claim 18, after "comprising" delete ";" and insert -- : --, therefor.

In column 23, line 30, in Claim 18, after "comparison" insert -- , --.

In column 24, line 4, in Claim 19, delete "indictor" and insert -- indicator --, therefor.

In column 24, line 10, in Claim 20, after "optical" insert -- inspection --.

UNITED STATES PATENT AND TRADEMARK OFFICE
CERTIFICATE OF CORRECTION

PATENT NO. : 7,171,037 B2
APPLICATION NO. : 10/393413
DATED : January 30, 2007
INVENTOR(S) : Mahon et al.

It is certified that error appears in the above-identified patent and that said Letters Patent is hereby corrected as shown below:

In column 24, line 19, in Claim 20, insert -- viewing angle of the -- before "image".

In column 24, line 28, in Claim 21, after "enhancing the" delete "viewing angle of the".

Signed and Sealed this

Twenty-second Day of January, 2008

JON W. DUDAS
*Director of the United States Patent and Trademark Office*